US 8,206,773 B2

(12) United States Patent
Ruberti et al.

(10) Patent No.: US 8,206,773 B2
(45) Date of Patent: Jun. 26, 2012

(54) NANOLOOM FOR CONTROLLING POLYMER ASSEMBLY

(75) Inventors: Jeffrey W. Ruberti, Lexington, MA (US); Gregory J. Kowalski, Beverly, MA (US); Daniel Burkey, Waltham, MA (US)

(73) Assignee: Northeastern University, Boston, MA (US)

( * ) Notice: Subject to any disclaimer, the term of this patent is extended or adjusted under 35 U.S.C. 154(b) by 1127 days.

(21) Appl. No.: 11/992,611

(22) PCT Filed: Sep. 27, 2006

(86) PCT No.: PCT/US2006/037681
§ 371 (c)(1),
(2), (4) Date: Mar. 26, 2008

(87) PCT Pub. No.: WO2007/038601
PCT Pub. Date: Apr. 5, 2007

(65) Prior Publication Data
US 2009/0148601 A1    Jun. 11, 2009

Related U.S. Application Data

(60) Provisional application No. 60/720,696, filed on Sep. 27, 2005.

(51) Int. Cl.
*A61L 33/00* (2006.01)
(52) U.S. Cl. ... 427/2.24; 264/40.7; 264/108; 264/171.1; 425/135; 427/256; 118/696; 530/356; 435/68.1
(58) Field of Classification Search ................ 427/2.24
See application file for complete search history.

(56) References Cited

U.S. PATENT DOCUMENTS

| 5,654,546 A | 8/1997 | Lindsay |
| 5,731,152 A | 3/1998 | Maracas et al. |
| 6,334,856 B1 | 1/2002 | Allen et al. |
| 6,582,393 B2 | 6/2003 | Sage, Jr. |
| 7,048,963 B2 | 5/2006 | Braithwaite et al. |
| 2003/0141618 A1 | 7/2003 | Braithwaite et al. |
| 2005/0019488 A1* | 1/2005 | Braithwaite et al. .......... 427/240 |
| 2006/0159722 A1 | 7/2006 | Braithwaite et al. |

OTHER PUBLICATIONS

Mosser et al., "Dense tissue-like collagen matrices formed in cell-free conditions", Matrix Biology, vol. 25 (2006), pp. 3-13.
Doleman et al., "Use of Compatible Polymer Blends to Fabricate Arrays of Carbon Black-Polymer Composite Vapor Detectors", Analytical Chemistry, vol. 70 (13) (1998), pp. 2560-2564.
Murthy et al., "Peptide Attachment to Vapor Deposited Polymeric Thin Films", Langmuir, vol. 20 (2004), pp. 4774-4776.
Anderson et al., "Mechanism of Osmotic Flow in Porous Membranes", Biophysical Journal, vol. 14 (1974), pp. 957-982.

(Continued)

*Primary Examiner* — Doris Lee
(74) *Attorney, Agent, or Firm* — Weingarten, Schurgin, Gagnebin & Lebovici LLP

(57) ABSTRACT

Systems, devices, and methods are provided for assembling polymer-forming molecular components such that highly-structured arrays of polymer strands, such as collagen fibrils, are formed without the need for cells. A polymer nanoloom is designed to control the self-assembly of monomers into fibrils and related tissue constructs including ligament, tendon, cartilage, and bone. A nanoloom system comprises a polymer printhead, a temperature controller, and a movable substrate for polymer printing. A polymer printhead contains one or more nanoreactors that can control the assembly of collagen fibrils or other polymers on a nanoscale. Methods are provided for temperature-driven, enzyme-driven, and cholesteric assembly of collagen or other polymers into two- or three-dimensional tissue constructs.

15 Claims, 13 Drawing Sheets

OTHER PUBLICATIONS

Guido et al., "A methodology for the systematic and quantitative study of cell contact guidance in oriented collagen gels", Journal of Cell Science, vol. 105 (1993), pp. 317-331.

Miyahara et al., "Formation of Collagen Fibrils by Enzymic Cleavage of Precursors of Type I Collagen in Vitro", Journal of Biological Chemistry, vol. 259 (15) (1984), pp. 9891-9898.

Wilson et al., "Surface organization and nanopatterning of collagen by dip-pen nanolithography", PNAS, vol. 98 (24), (2001), pp. 13660-13664.

Miyahara et al., "Formation of Collagen Fibrils in Vitro by Cleavage of Procollagen with Procollagen Proteinases", Journal of Biological Chemistry, vol. 257 (14) (1982), pp. 8442-8448.

Wood et al., "The Formation of Fibrils from Collagen Solutions", Biochemical Journal, vol. 75 (1960), pp. 588-598.

Williams et al., "Collagen Fibril Formation", Journal of Biological Chemistry, vol. 253 (18) (1978), pp. 6578-6585.

Brown et al., "Ultrarapid Engineering of Biomimetic Materials and Tissues: Fabrication of Nano- and Microstructures by Plastic Compression", Advanced Functional Materials, vol. 15 (2005), pp. 1762-1770.

Sahoo et al., "Characterization of a Novel Polymeric Scaffold for Potential Application in Tendon/Ligament Tissue Engineering", Tissue Engineering, vol. 12 (1) (2006), p. 91-99.

Lee et al., "Blood Compatibility of Polyethylene Oxide Surfaces", Progress in Polymer Science, vol. 20 (1995), pp. 1043-1079.

Prime et al., "Adsorption of Proteins onto Surfaces Containing End-Attached Oligo(ethylene oxide): A Model System Using Self-Assembled Monolayers", Journal American Chemical Society, vol. 115 (1993), pp. 10714-10721.

Malmsten et al., "Effect of Chain Density on Inhibition of Protein Adsorption by Poly(ethylene glycol) Based Coatings", Journal of Colloid and Interface Science, vol. 202 (1998), pp. 507-517.

Hulmes, "Building Collagen Molecules, Fibrils, and Suprafibrilar Structures", Journal of Structural Biology, vol. 137 (2002), pp. 2-10.

Besseau et al., "Stabilization of Fluid Cholesteric Phases of Collagen to Ordered Gelated Matrices", J. Mol. Biology, vol. 251 (1995), pp. 197-202.

Lee et al., "Protein-resistant coatings for glass and metal oxide surfaces derived from oligo(ethylene glycol)-terminated alkyltrichlorosilanes", Biomaterials, vol. 19 (1998), pp. 1669-1675.

Ruberti et al., "Strain-controlled enzymatic cleavage of collagen in loaded matrix", Biochemical and Biophysical Research Communications, vol. 336 (2005), pp. 483-489.

Birk et al., "Fibroblasts Create Compartments in the Extracellular Space Where Collagen Polymerizes into Fibrils and Fibrils Associate into Bundles", Annals of the New York Academy of Sciences, vol. 460 (1985), pp. 258-266.

Knight et al., "In Vitro formation by reverse dialysis of collagen gels containing highly oriented arrays of fibrils", J. Biomed. Mater. Res., vol. 41 (2) (1998), pp. 185-191.

Cassel, "Collagen Aggregation Phenomena", Biopolymers, vol. 4 (1966), pp. 989-997.

Dufrêne et al., "Influence of Substratum Surface Properties on the Organization of Adsorbed Collagen Films: In Situ Characterization by Atomic Force Microscopy", Langmuir, vol. 15 (1999), pp. 2871-2878.

Freed et al., "Biodegradable Polymer Scaffolds for Tissue Engineering", Bio/Technology, vol. 12 (1994), pp. 689-693.

Prime et al., "Self-Assembled Organic Monolayers: Model Systems for Studying Adsorption of Proteins at Surfaces", Science, vol. 252, pp. 1164-1167.

Sofia et al., "Poly(ethylene glycol) Chemistry and Biological Applications: Protein Adsorption on Poly(ethylene oxide)-Grafted Silicon Surfaces", American Chemical Society, vol. 680 (1997), pp. 342-360.

Holmberg et al., "Immobilization of Proteins via PEG Chains", Poly(Ethylene Glycol) Chemistry: Biotechnical and Biomedical Applications (1992), pp. 303-324.

\* cited by examiner

NANOLOOM FOR CONTROLLING POLYMER ASSEMBLY

CROSS REFERENCE TO RELATED APPLICATIONS

This application claims the priority of U.S. Provisional Application No. 60/720,696 filed Sep. 27, 2005 entitled, NANOLOOM FOR CONTROLLING POLYMER ASSEMBLY, the whole of which is hereby incorporated by reference herein.

STATEMENT REGARDING FEDERALLY SPONSORED RESEARCH

The invention was made with support from National Science Foundation Grant CMS-0541707. The United States Government has certain rights in the invention.

BACKGROUND OF THE INVENTION

During collagen synthesis by fibroblasts, cell-mediated assembly of collagen fibrils takes place in cell-surface crypts (FIG. 1A). The crypts are typically located on one pole of the synthetically active cell. Matrix components, including collagen are transported to the crypts, assembled and secreted into the extracellular space by vectorial discharge (FIG. 1B).

Within the crypts, individual procollagen molecules are prepared for self-assembly by enzymatic cleavage of their N- and C-terminal propeptides. Once these are cleaved, the remaining tropocollagen monomer (~300 nm in length) will spontaneously self-assemble into secondary aggregate polymeric fibrils, which display the classic quarter-stagger arrangement. In vivo, the temperature and pH in the crypt are conducive to self-assembly. Thus, the rate of fibril formation is then likely to be dependent on the transport of procollagen to the crypt.

Typically, engineered connective tissue constructs are initiated by seeding fibroblast cells into a self-assembled collagen gel. However, such constructs typically do not contain collagen fibrils with sufficient order and typically do not have the load-bearing capacity of biological tissues.

There are few devices designed to construct collagen arrays that are ordered on the nanoscale. However, there have been some attempts, which are described below.

In one approach, some early researchers attempted to control collagen fibril orientation during fibrillogenesis by applying a large magnetic field to the vessel in which assembly was taking place (Guido et al., 1993). However, using a bulk magnetic field to align collagen fibrils during fibrillogenesis does not produce a high degree of alignment, nor does it allow control of orientation within the bulk collagen matrix that is generated.

In a more recent patent application, Braithwaite and Ruberti describe a method by which collagen fibrils can be aligned in sheets within a thin shear film (US patent application 20030141618). Alignment of the collagen fibrils is excellent, but the method is difficult to use due to the instability of the thin shear film and the problems associated with constructing multiple layers to produce a three-dimensional template. In addition, the constraint of assembly in a shearing flow places limitations on the ability to transport and allow binding of additional components during the self-assembly of the fibrils.

Braithwaite and Ruberti also describe a collagen nanoloom device. This device uses microfluidic driving forces to bring together the reacting molecules. In this system, collagen fibrils might form but would be uncontrollably driven from the nanoreactors by the exiting fluid flow. Further, the device, as depicted, draws fibrils from the reactors by moving away from a surface (to which formed collagen fibrils have adhered). Such a design would require that the "loom" always be tethered directly to this surface by a straight line of extruded collagen, which limits the ability of the system to produce patterns.

Finally, Wilson et al., 2001, describe a method of precisely placing collagen onto a substrate using dip pen nanolithography. This method requires the use of an atomic force microscope (AFM) type head and would require massive modification to produce large arrays of fibrils in three dimensions.

Thus, there remains a need for a system of devices and corresponding methods capable of producing two- and three-dimensional arrays of collagen fibrils and other polymer strands in a desired pattern. Such patterned arrays are important components for producing artificial cornea, tendon, bone, and other tissues and structures, particularly those involving extracellular matrix proteins.

BRIEF SUMMARY OF THE INVENTION

The invention provides an array of nano to microscale reactors designed to contain and control the arrival and availability of polymer-forming molecular components such that highly-structured arrays of polymer strands may be produced. For the purposes of description, the preferred embodiment for this invention is a collagen nanoloom, which is designed to control the self-assembly of collagen monomers into fibrils and related tissue constructs including ligament, tendon, cartilage, and bone. However, the principles of operation apply to any self-assembling or polymerizing biopolymer or polymeric system. For the preferred embodiment, it is noted that under the correct conditions, collagen monomers will self-assemble into intermediate filaments or into fully formed collagen fibrils. The reactor design not only controls the rate of self-assembly of collagen into fibrils, it provides a mechanism to precisely size and space the collagen fibrils that are produced. The invention, through precise motion control, also provides a means for modulating the residence time of forming fibrils in the reactor and then drawing self-assembled fibrils from the reactors (which is a particularly important feature). The invention provides the ability to control the transport rate of monomer to the reaction zone and will allow functionalization of the reactor surface to control interaction with monomers and formed polymers.

One aspect of the invention is a system for the patterned deposition of a polymer by self-assembly. The system comprises a polymer printhead, a temperature controller, and a substrate. The polymer printhead comprises a monomer solution reservoir and a microcolumn that is fluidically coupled at a loading end to the reservoir. The temperature controller regulates temperature within the microcolumn, either as a constant temperature throughout the microcolumn or as a gradient of increasing temperature from the loading end to the elution end of the microcolumn. The substrate is mounted in apposition to the elution end of the microcolumn and is movable in a plane orthogonal to the axis of the microcolumn. A polymer of the monomer is deposited onto a surface of the substrate apposed to the microcolumn.

Another aspect of the invention is a method of forming aligned polymer strands by temperature-dependent self assembly. The method comprises providing a reservoir containing a cold (0-15° C.) monomer solution, causing the solution to flow through a microcolumn having a temperature gradient (0-15° C. at the loading end to 25-50° C. at the elution end) that allows monomers to self-assemble in the microcolumn, and eluting polymer strands from the microcolumn onto a moving substrate. The substrate, which is apposed to the elution end of the microcolumn, comprises a patterned distribution of binding sites for the polymer strands.

Yet another aspect of the invention is a method of forming aligned polymer strands by enzyme-dependent self-assembly. The method comprising providing a reservoir containing a solution of a monomer precursor protein, causing the solution to flow through a microcolumn, and eluting the solution onto a moving substrate. The substrate is bathed in a solution comprising an enzyme that cleaves the monomer precursor protein, resulting in the formation of polymer strands and their deposition on the substrate.

Still another aspect of the invention is a method for the temperature-dependent cholesteric assembly of collagen fibrils. The method comprises providing a reservoir containing a solution of monomeric collagen, causing the solution to flow through a microcolumn, eluting the monomeric collagen into a confined space between the elution end of the microcolumn and a substrate, and osmotically concentrating the monomeric collagen to 5.0-1000.0 mg/ml, leading to cholesteric assembly of collagen fibrils. The substrate comprises a dialysis membrane enclosing an osmicant solution having an osmotic pressure higher than that of the monomeric collagen solution. In some embodiments, the monomer is procollagen, and the substrate comprises one or more enzymes capable of cleaving C- and N-terminal propeptides of the procollagen monomer, resulting in cholesteric assembly of collagen fibrils.

BRIEF DESCRIPTION OF THE DRAWINGS

Other features and advantages of the invention will be apparent from the following description of the preferred embodiments thereof and from the claims, taken in conjunction with the accompanying drawings, in which:

DETAILED DESCRIPTION OF THE INVENTION

In a preferred embodiment, the invention provides systems of devices and methods of using such systems to "print" two- and three-dimensional, highly-organized collagen templates from nanoscale reactors for use in tissue engineering. Further, arrays of such nanoreactors can be assembled into a moving "nanoloom," allowing fibril spacing and alignment to be controlled as well.

Purified, extracted, acid-soluble collagen monomers (tropocollagen) will self-assemble into fibrils at 37° C. and neutral pH. The systems and methods of the invention mimic the function of cell surface crypts in a "nanoreactor," resulting in control over collagen fibrillogenesis.

Figure 1A:
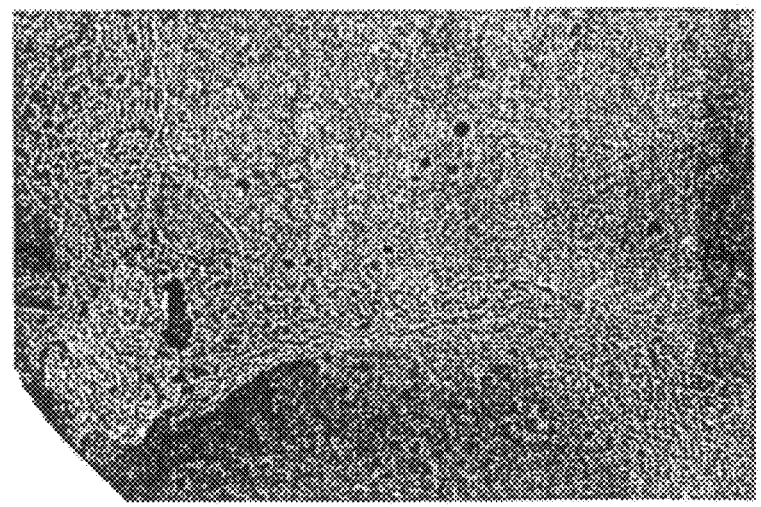
FIGS. 1A and 1B are quick-freeze deep etch micrographs of synthetically active human corneal fibroblasts in culture showing (FIG. 1A) a corneal fibroblast displaying linear arrays of surface crypts and (FIG. 1B) a close up image of collagen vectorial secretion into extracellular space (arrow)
Figure 1B:
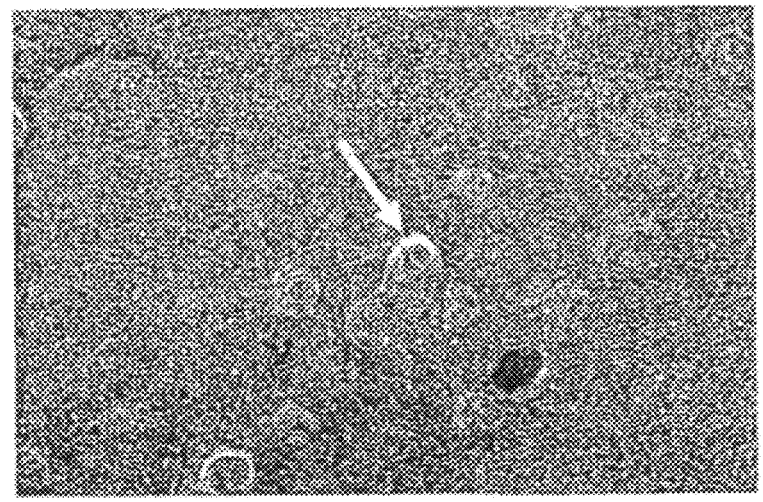
Figure 2:
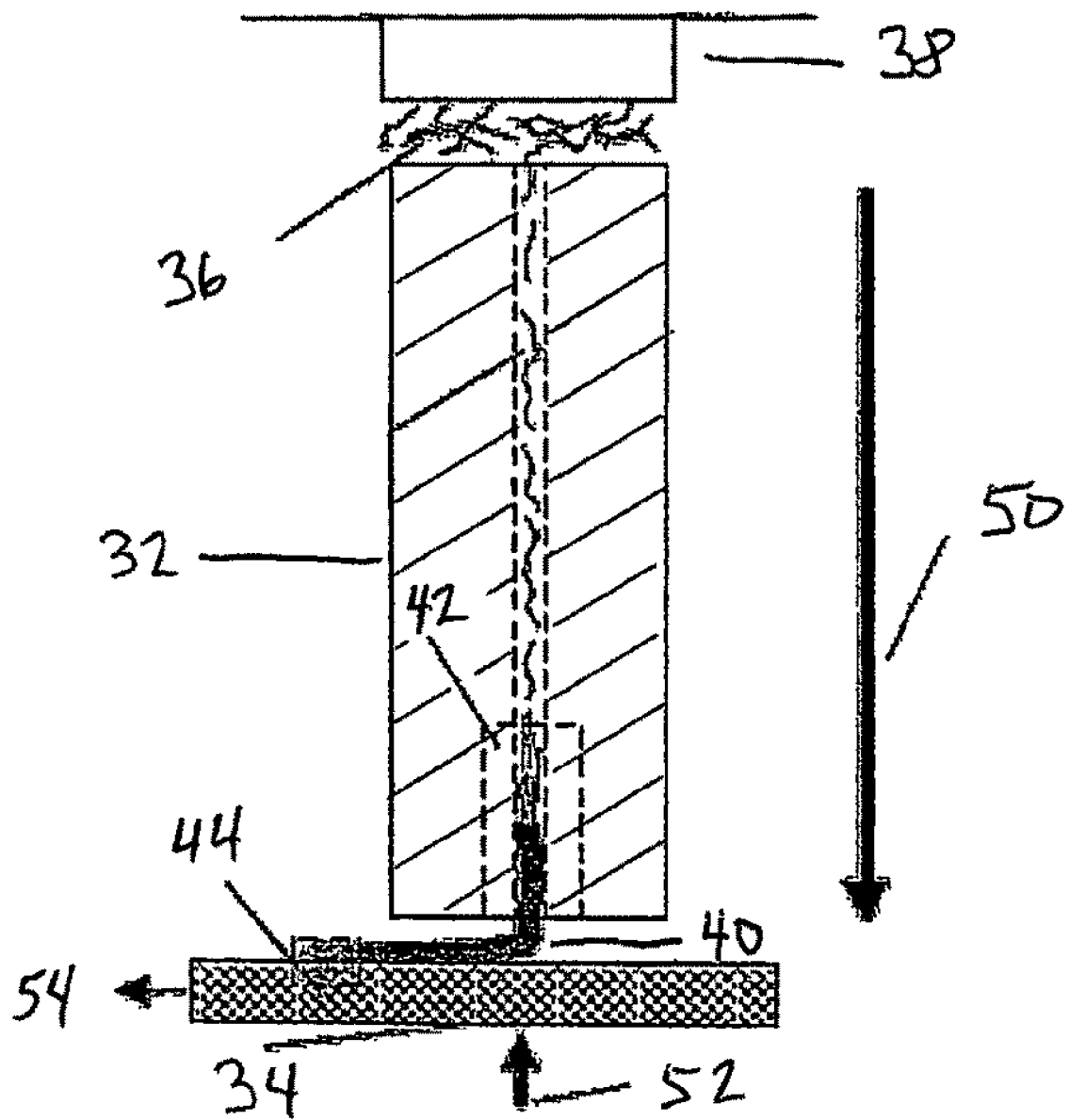
FIG. 2 is a schematic of an individual nanoreactor or microcolumn in a preferred embodiment nanoloom system according to the invention for collagen fibrillogenesis in vitro.
Figure 3:
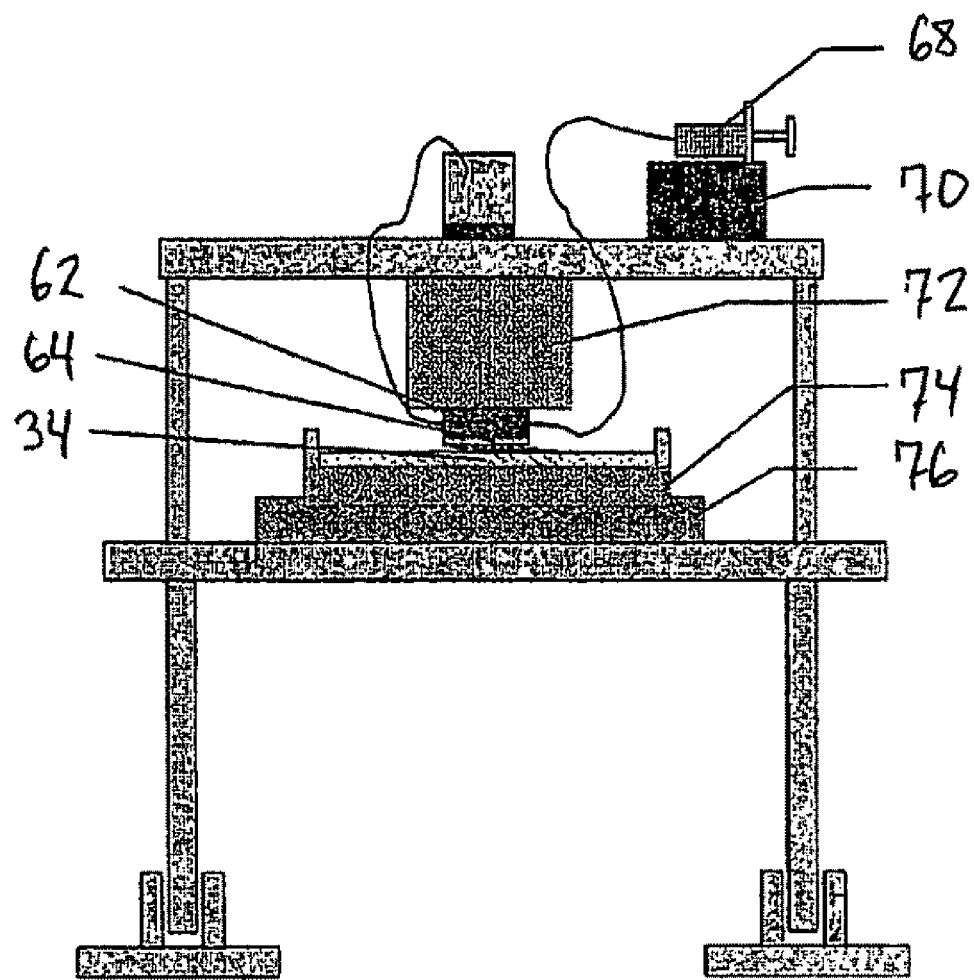
FIG. 3 is a schematic showing a preferred embodiment of an integrated nanoloom system according to the invention incorporating the individual nanoreactor of FIG. 2.
Figure 4:
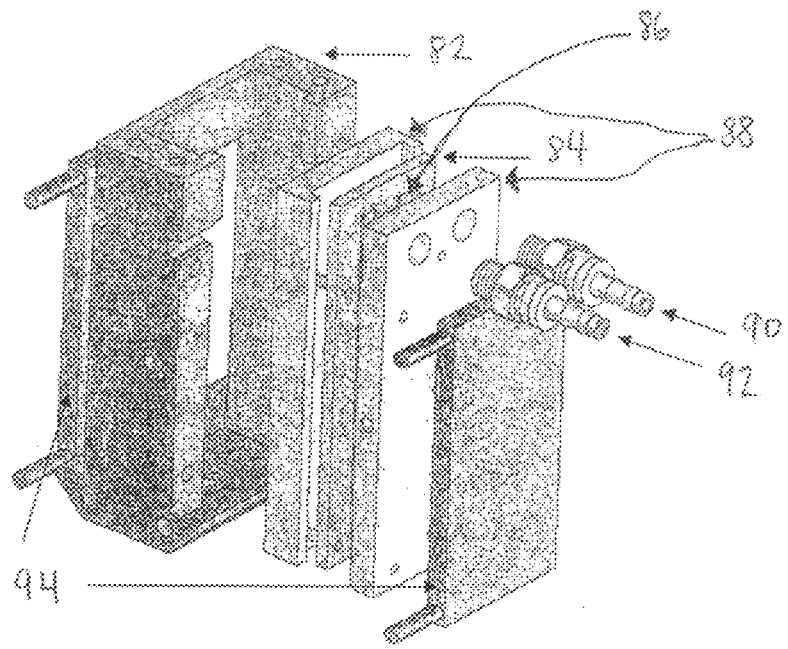
FIG. 4 is an isometric exploded view of one embodiment of a temperature controller for a nanoloom printhead in the system of FIG. 3.
Figure 5:
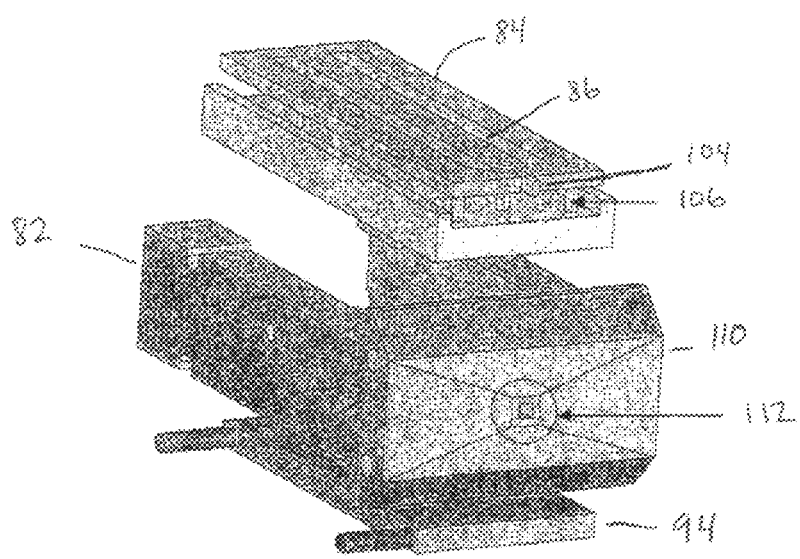
FIG. 5 is an isometric exploded view of one embodiment of a nanoloom printhead.
Figure 6:
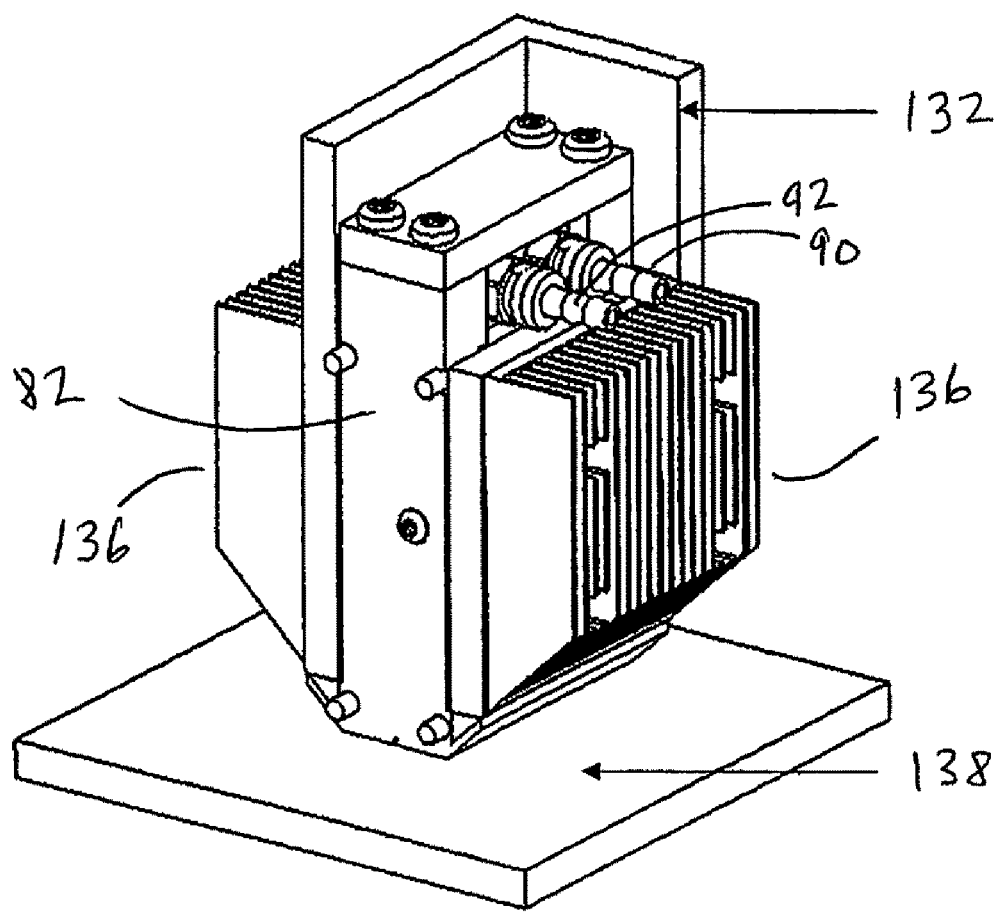
FIG. 6 is an isometric view of one embodiment of an assembled nanoloom head with temperature controller and substrate stage.

Referring to FIGS. 2 and 3, in one embodiment, a nanoloom comprises a number of functionally distinct components: (1) multiple nanoreactors 32, 64, in a "polymer printhead" 62; (2) a substrate 34 onto which polymerized molecules are printed and attach to polymer binding sites 44; and (3) a precision motion-controlled gantry 76 (see also 132 and 138 in FIG. 6), which provides the relative motion 54 and force 52 between the first two components. Other important components include a reservoir 62 for a solution of monomers to be polymerized and various temperature controllers 38, 72, 74 to regulate the temperature of the monomer solution 36 and the polymer assembly area 42, and to establish a temperature gradient 50 along the nanoreactor.

The first component is the polymer printhead, as shown in FIGS. 4-8, which contains one or more nanoreactors; arrays of nanoreactors are preferred. The nanoreactors, which can be similar in scale to cell surface crypts, can be pores or "microcolumns" that traverse a membrane. A track-etched polycarbonate sheet forms a preferred array of microcolumns. The membrane 112 containing the microcolumns is mounted in a printhead 100 at a membrane attachment site. The printhead also provides a reservoir 86 for reactants. Typical reactants include monomers of the polymers to be deposited on a substrate, a buffer solution suitable for maintaining the monomers in a stable monomeric state and for promoting later polymer formation, catalysts (e.g., enzymes) or other components necessary to promote (or initially inhibit) the polymerization, accessory molecules such as proteins that promote polymerization or ordering of the polymer arrays, and mechanical modifiers, such as hydroxyapatite or cross-linking reagents, to provide desired properties, such as mechanical rigidity, elasticity, or stability to the polymer construct. Some of these reactants may be provided in subsidiary reservoirs so that the timing of their additions maybe controlled separately.

In some embodiments, the reservoir is temperature controlled. The printhead, in certain embodiments, may also be capable of providing pressure and/or voltage to one side of the microcolumn for the purposes of driving reactants through the column. In some embodiments, collagen self-assembly can be facilitated in the reactor chamber (i.e., within the microcolumn) by providing precise control of the temperature and, optionally, the pH. The temperature of the monomer reservoir will be kept well below 30° C. (e.g., 0°-30° C., 0-15° C., or 0°-10° C.) to prevent premature self-assembly. In addition, the pH may also be maintained in a range (e.g., 2.0-7.2 for collagen) selected to prevent premature self-assembly of the fibrils. The monomer diffusion rate from the reservoir to the assembly (reaction zone of the microcolumn, or the space outside the elution end of the microcolumn in certain embodiments) can be controlled by the microcolumn width, the microcolumn length, the fluid connection between the reservoir and the microcolumn, the hydrostatic pressure in the reservoir or at the loading end of the microcolumn, and the monomer concentration (e.g., through viscosity effects of the monomer or other components of the monomer solution).

Referring again to FIGS. 4-6, in one embodiment, the polymer printhead contains a temperature controller 80 with control elements 94 for both the monomer solution reservoir 86 as a whole and the loading end of the microcolumn or microcolumn array 112. Cooled monomer solution can be flowed through the head from a supply container (such as a supply syringe 68 attached to a pump 70, as shown in FIG. 3) by means of the inlet and outlet ports 90, 92. The reservoir 86 can be formed by spaces in a gasket 84 mounted within a thermoconductive housing 88, which in turn can be cooled by thermoelectric coolers 94 (e.g., Peltier devices). Heat sinks 136 improve the effectiveness of the thermoelectric coolers. The entire printhead can be mounted to a gantry via a mounting bracket 132 attached to an isolative mounting bracket 82 that surrounds the reservoir and its temperature controller. A precision stage Z-axis controller can be attached to the mounting bracket, and an X-Y controller can drive substrate stage 138.

Figure 7:
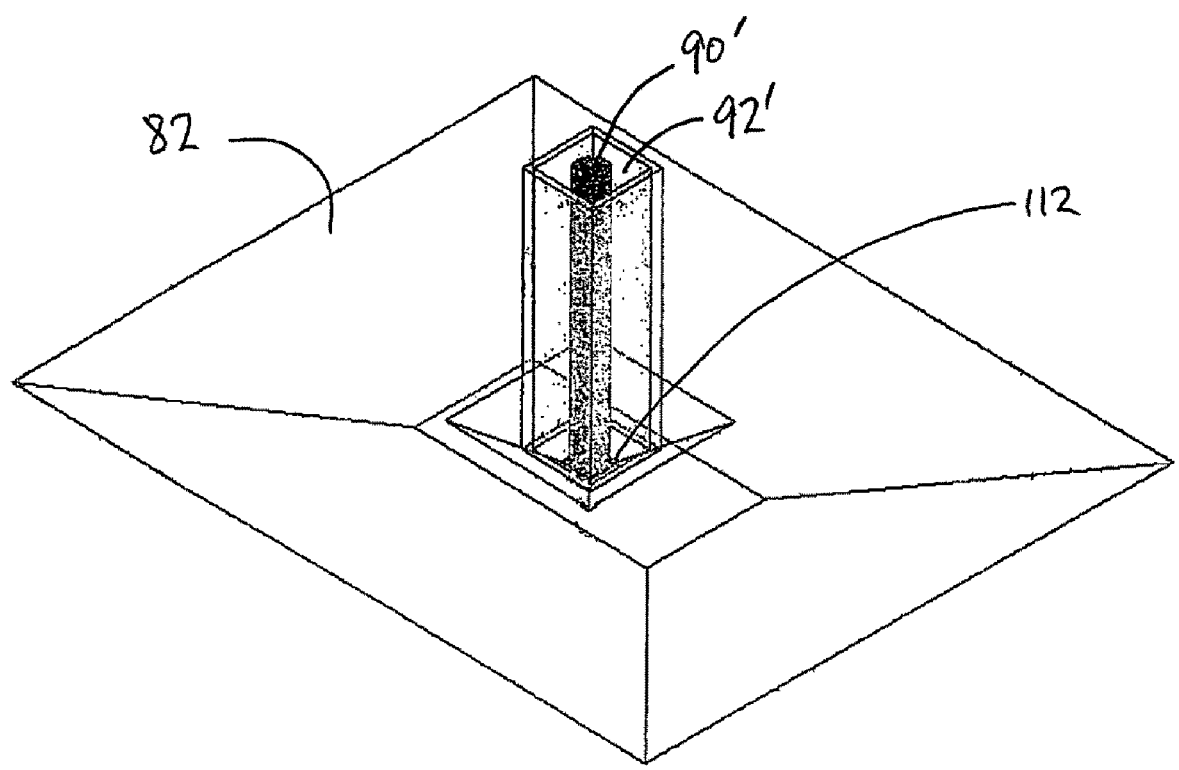
FIG. 7 is an isometric transparent inside view of one embodiment of nanoloom printhead showing the monomer solution reservoir.
Figure 8:
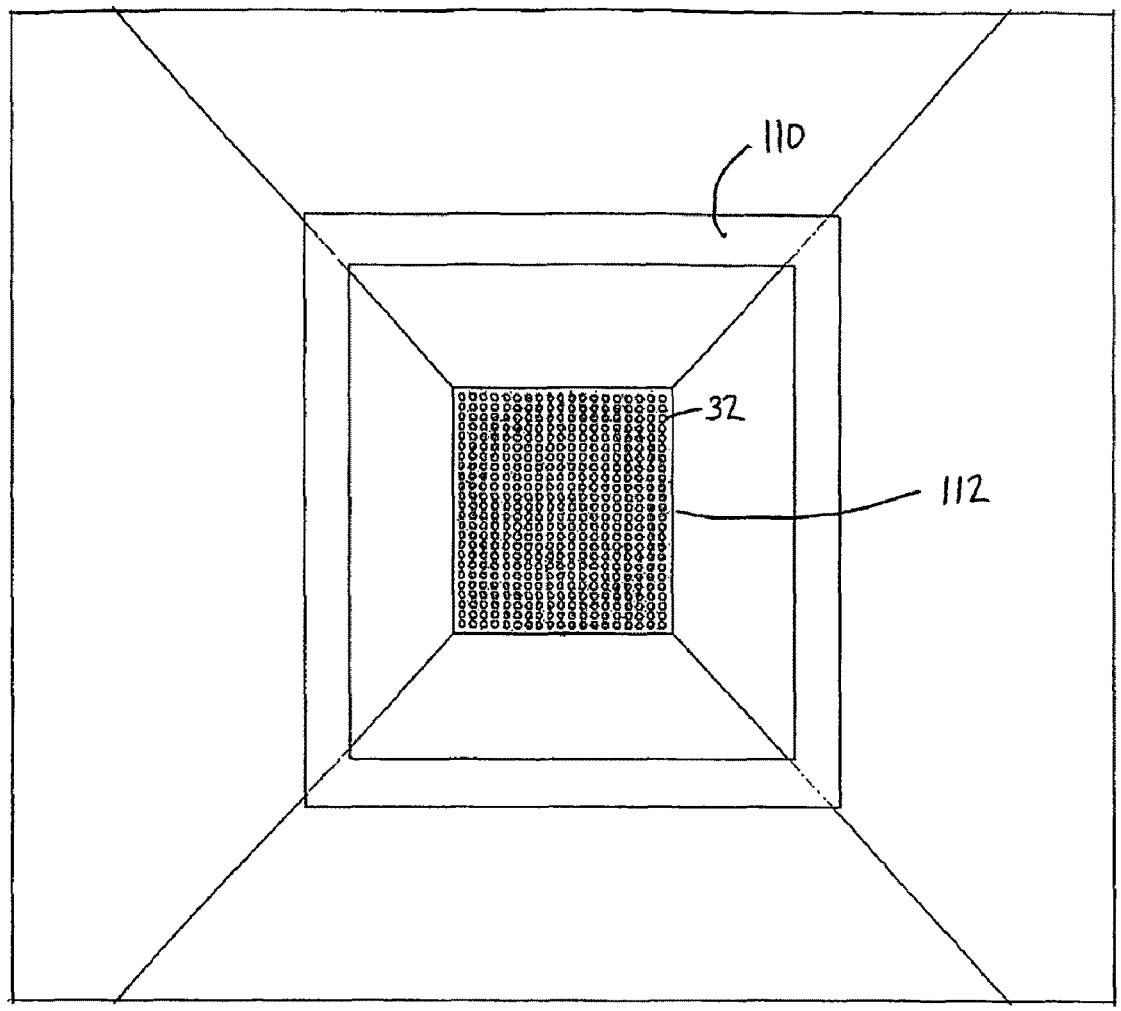
FIG. 8 is an isometric view of one embodiment of a nanoloom printhead showing the printing surface with attached microcolumn array.

Another embodiment of the polymer printhead is depicted in FIGS. 7 and 8. FIG. 7 is an interior view of the printhead showing the lower portion of isolative mounting element 82 and the loading end of microcolumn array 112. The monomer solution reservoir within the printhead is composed of two components, an inlet tube 90', which is connected to inlet port 90 and delivers the monomer solution at a controlled temperature (e.g., 4° C.) to the loading end of microcolumn array 112, and an over-flow or outlet tube 92', which is oriented concentrically around inlet tube 90' and is connected to outlet port 92. FIG. 8 is an exterior view of the printhead showing a microcolumn array, which may take the form, e.g., of a track-etch membrane, and contains individual microcolumns or pores 32, such as shown schematically in FIG. 2.

The second component of the polymer printhead is the substrate 34 onto which the polymers are printed. The rate of polymer extraction can be controlled by the translation of the substrate, which can be pressed against the nanoloom exit pores, i.e., the microcolumn elution end. The substrate may or may not be patterned or coated with molecules that bind the formed polymers after they exit the microcolumn. The substrate functions both to prevent premature exit of unpolymerized monomers and to provide a means to draw polymerized filaments from the microcolumn arrays at controlled rate. As will be described in more detail below, FIG. 2 shows a schematic of a portion of a system for patterned polymer deposition. For most applications the substrate will move perpendicular to the pore long axis, (as shown in FIG. 2). However, other relative motions between the substrate and the microcolumn arrays are possible. The substrate can be integrated into a device that provides precise motion and temperature control and that may also provide an electrical potential or negative pressure designed to draw polymers from the microcolumn.

The third component of the printhead is the motion control system. To generate arrays of aligned polymers that have emerged from the microcolumn, the substrate and printhead can be integrated into a precision motion-controlled gantry 76. The components of the gantry interface with the printhead by means of one or more rigid mounting brackets 132 and with the substrate by means of a solid platform 138 to which the substrate is attached or upon which the substrate rests. The gantry can provide relative motion between the substrate and the microcolumn such that the polymerized filaments may be "drawn" from the reactors at an appropriate rate. In addition, the gantry allows for the force perpendicular to the substrate plane and aligned with the microcolumn axis to be controlled as well. FIG. 3 shows one embodiment of an integrated gantry motion-control arrangement. Though FIG. 2 indicates the motion between the substrate and the printhead is two-dimensional and planar, the substrate can be any shape, and the motion control system can be designed to produce complex three-dimensional motions.

For the purposes of controlling polymer formation, the invention allows control over several fundamental parameters. The length of a nanoreactor pore or microcolumn can be in the range of 1-100 microns; preferred lengths are 6-15 microns. The pore diameter of a nanoreactor or microcolumn can be in the range of 5 nm to 4 microns, and preferably is in the range of 70-90 nm. The spacing of nanoreactor pores or microcolumns in an array can be in the range of 5 nm-10 microns between any two adjacent pores or microcolumns. Track-etched membranes, which can be employed as microcolumn arrays, generally have a pore density of $1\times10^4$-$1\times10^9$ pores/cm$^2$. The relative motion of the printhead and the substrate (i.e., gantry velocity) can be in the range of 100 nm-10 microns per sec. The orthogonal force of the substrate on a nanoreactor array can be in the range of 0.001-100 N. The pressure drop across a nanoreactor or a nanoreactor array can be 0-1000 PSI. The electrical potential drop across a nanoreactor or nanoreactor array can be $10^{-5}$-10 V. The concentration of reactants and other polymerization components is generally as follows (but see further details presented below): collagen or other monomer, 0.1-1000 mg/ml; polyethylene glycol (PEG) or other osmicant, 0.1-50.0% (wt/vol); proteoglycans, 0.1-20.0% of collagen weight; temperature of reservoir, 0° C.-100° C.; and temperature of substrate, 0° C.-100° C.

The nanoloom system is capable of printing polymer arrays in virtually any shape in two and three dimensions, with a resolution as small as one fibril or polymer strand diameter or as large as hundreds of thousands of fibril diameters. Resolution depends on the number of functioning nanoreactors (microcolumns) in the array and the size and spacing of the individual nanoreactors.

The ability to precisely control fibril assembly within a microcolumn while preventing the premature exit of the fibril is accomplished by apposing the microcolumn opening at the elution end against a moving substrate. This feature allows control of the residence time of the forming fibrils such that monomers arriving from the monomer reservoir can be incorporated. Optionally, fibril residence can be controlled in addition by the use of hydrostatic pressure (either positive or negative, positive preferred) applied to the monomer solution reservoir or to the loading end of the microcolumn, and counter pressure (either positive or negative, negative preferred) applied to the substrate in the direction of the elution end of the column.

The coupling of the microcolumn to a precision motion control system not only enables the system to "print" two- and three-dimensional polymer matrices, it also allows the user to "draw" polymerized fibrils from the microcolumn at a rate that matches their assembly. Furthermore, the motion control system permits fibrils to be aligned into parallel arrays and to be stacked in three-dimensional arrangements of alternating layers by successive printing over already formed fibrils.

A polymer printhead is fluidically coupled with, and preferably incorporates, a reservoir for the solution of monomers that eventually are converted to the corresponding polymers. The reservoir is a container for solutions, preferably aqueous solutions, and has an inflow access port, optionally connected with a bulk supply of monomer solution for refilling, and an outflow access port, optionally connected to a waste receptacle or back to the bulk supply of monomer solution, e.g. via a pump. Depending on the volume of monomer solution contemplated for a given use, it can be advantageous to connect the monomer solution reservoir to a monomer solution supply which is preferably located outside the printhead. For example, monomer solution from a supply container (e.g., a bottle or syringe) can be circulated through the reservoir in the printhead using a pump (e.g., a peristaltic or syringe pump); preferably the monomer solution is temperature-controlled at a low temperature (e.g., 4° C.) so as to prevent polymerization. Alternatively, the monomer solution can be entirely contained within the printhead, in which case access is provided in the printhead for refilling the reservoir. The reservoir or a portion thereof is fluidically connected to the loading end of a microcolumn. Materials for constructing the reservoir should be thermally conductive and corrosion resistant. Suitable materials include stainless steel and polymer-coated, highly conductive metals (e.g., copper, silver, gold). The geometry of the reservoir can be chosen to suit the physical location, volume requirements, temperature control requirements, and proximity to the microcolumn of a particular device or system. Preferably, the reservoir is connected to one or more microcolumns by means of a tube, channel, or other fluid interface fabricated within the polymer printhead.

One or more additional solution reservoirs optionally can be used with the polymer printhead (nanoloom) system. For example, if there is the need for exchanging or mixing solutions on the microcolumn, or producing a gradient of one or more solution components on the column, then a second, third, or further solution reservoirs can be added, optionally connected via tubing or another fluid transport structure to a pump or gradient former, and then to the loading end of the microcolumn. Additional solution reservoirs may be useful, for example, for establishing a gradient of pH, ionic strength, or monomer concentration, for separating solutions containing different components (e.g., different monomers), or for washing the microcolumn.

The solution in the monomer solution reservoir is generally an aqueous buffer solution that can contain any mixture of molecules that will undergo self-assembly when exposed to either a rise in temperature, a change in pH (optionally combined with a rise in temperature), or upon exposure to a catalyst (e.g., cleavage by an enzyme or exposure to component such as a binding or accessory protein, such as a proteoglycan). The solution in the reservoir may also contain mixtures of such molecules and molecules that are thought to control the self-assembly process (e.g., NaCl or other salts or metal ions). In addition, solutions containing assembling molecules may be alternated with solutions of control molecules in a prescribed sequence and in any order.

Coupling the monomer reservoir to a fluid control system allows the rapid and controlled manipulation of monomer concentration and also allows the addition of new chemical components while printing a polymer matrix. Gradients in space can be printed by altering the concentration of collagen or by adding other components. For example, the addition of hydroxyapatite crystals to the monomer reservoir allows the nanoloom system to gradually transition from the printing of tendon to the printing of bone. Cross-linking agents and polymer binding proteins can also be added using the appropriate solutions and optional additional reservoirs.

Any monomer that is capable of self-assembly triggered by a shift in temperature, pH, or addition or modification of a chemical component (e.g., by enzyme cleavage), can be used in the invention. Such monomers can be either naturally occurring molecules or synthetic. Monomers that assemble to form linear polymer strands or fibrils are preferred. Preferred thermally triggered self-assembling monomers for use in the invention include neutralized extracted collagen type I (e.g., PureCol™ by Nutracon); any neutralized acid-extracted collagen of types I, II, III, or V; any pepsin-extracted collagen of types I, II, III, or V; and any collagen of type I, II, III, or V isolated from cell culture (including recombinant collagens), preferably where the N- and C-terminal propeptides are intact. Collagen or other monomer substances can be isolated from natural sources or produced synthetically, e.g., using recombinant methods.

Preferred fibrillogenesis control molecules, which may be added to either the monomer solution or another solution in the monomer solution reservoir, an additional reservoir, or present on the substrate, include proteoglycans such as decorin, lumican, biglycan, or aggrecan, and glycosaminoglycans such as chondroitin sulfate, dermatan sulfate, or keratan sulfate.

A polymer printhead contains one or more microcolumns, which are small fluid chambers that have a length-to-width aspect ratio greater than one and are coupled at a loading end to one or more solution reservoirs, including at least a monomer solution reservoir, and at the elution end to a gap between the column and a polymer deposition substrate. In certain embodiments, the assembly of monomers to polymer occurs within the microcolumn. In other embodiments, the assembly of monomers to polymer occurs after the monomer solution has been eluted from the microcolumn. In preferred embodiments, an array of microcolumns is used, with each microcolumn in the array being coupled at its loading end to a common monomer solution reservoir and at its elution end to the gap between the columns and a common substrate apposed to the elution ends of the columns. Microcolumns in an array are preferably aligned such that their loading ends and their elution ends are in register. Microcolumns in an array are preferably co-planar, and their long axes are preferably parallel. If the columns are present in a common planar structure, the microcolumn array can be a membrane, such as a track-etched membrane. In certain embodiments, the microcolumn array can be a fiber filter, such as a glass fiber filter or a polymer (e.g., nitrocellulose) filter. The dimensions of a microcolumn can vary from 1-100 microns in length and from 5 nm to 4 microns in diameter.

Temperature within a microcolumn is controlled by a temperature controller suitable for providing either a constant temperature within the column or in some embodiments for providing a temperature gradient across the length of the column. Preferably the temperature in the column is constant to within 0.1, 0.5, 1, 2, 5, or 10° C. if a constant temperature is desired within the column. Gradients of temperature can be in either direction, but preferred are gradients starting from a temperature in the range of 0-15° C. at the loading end to a temperature in the range of 25-50° C. at the elution end.

Especially preferred is a gradient from 2-4° C. at the loading end to 35-40° C. at the elution end. Gradients can be either linear or non-linear. The actual temperature at any given position in the column can vary from the theoretically predicted value for a desired gradient by 0.1, 0.5, 1, 2, 5, 10, or 15° C., depending on the accuracy required by a particular method. Temperature control is described further below.

Track-etched membranes are low cost polymer-based membranes used commonly in the cell culture industry. They are typically made by exposing a thin film of a material such as polycarbonate to high energy charged particles to create "tracks" in the material which are then chemically etched to create highly uniform cylindrical pores. Pore size can vary from about 20 nm to at least four microns and is determined by the etching procedure. Track-etched membranes are typically thin, ranging from a few microns (e.g., one to six microns) to about 15-20 microns in thickness, though this fact is not intended to limit the length of any microcolumn used in the invention. Typical track-etched membrane materials include polycarbonate and polyester, both of which are highly biocompatible and do not readily adsorb polymers such as proteins. Polycarbonate is neutral with regard to hydrophobicity, and polyester is naturally hydrophilic. Unlike polyester membranes, polycarbonate membranes can be functionalized because of the presence of carboxyl groups. The pore density of track-etched membranes ranges from $1 \times 10^4$ to $1 \times 10^9$ pores/cm$^2$. A pore density corresponding to a 20% pore areal fraction is preferred, but can be in the range of 5-40%.

The interior of the microcolumn is preferably chemically derivatized so as to reduce or eliminate the binding of the monomers, the polymers of the monomer, or both to the interior surface of the column. The exterior face of the column at the elution end, e.g., the elution face of a track-etched membrane, can also be derivatized in this manner.

For example, the attachment of poly(ethylene glycol) (PEG) onto surfaces is a facile way to prevent protein adsorption, based on its well-known biological non-adhesiveness. (See Lee et al., 1998; Malmsten et al., 1998; Prime et al., 1993; Prime et al., 1991; Lee, J. H. et al., 1995; and Sofia et al., 1997). The biological non-adhesiveness of PEG can be explained in terms of steric stabilization and solution properties of PEG in water.5 The steric stabilization effect has two components; an elastic term and an osmotic term. (Lee et al., 1998 and Holmberg et al., 1992). When a cell or protein approaches the PEG-grafted surface, total number of conformations available to the PEG chains is reduced, resulting in a loss in configurational entropy. This loss is reflected in the elastic term. The osmotic term describes the repulsive force generated by the compression or interpenetration (or both) of the PEG chains by the approaching protein or cell. The unique behavior of PEG, however, cannot be explained by steric stabilization alone. The second mechanism for non-adhesiveness is related to the solubility of PEG in water. Due to the structural similarity of the PEG repeat units and water molecules, chains of PEG are easily accommodated in water lattices without steric hindrance. PEG chains in aqueous solutions are therefore hydrated and highly mobile, and will tend to prevent any approaching cells or proteins from contacting the underlying surface. All of the above effects, namely configurational entropy loss, osmotic repulsion, and chain mobility, are enhanced by increasing chain length. Longer PEG chains would thus be expected to show a greater resistance to protein adsorption and cell adhesion.

A polycarbonate track-etched membrane can be derivatized with PEG as follows. Polycarbonate polymer consists of an alkyl backbone chain with pendant carboxylic acid groups. These groups can be tethered to amine groups on any polymer or peptide molecule using the well-known carbodiimide coupling reaction. (Murthy et al., 2004). The carbodiimide molecule binds to the carboxylic acid group to form a reactive intermediate. This intermediate then reacts with any available primary amine group on the peptide to form an amide bond between the PC chain and the polymer or peptide. Carbodiimde is generated as a by-product. PEG attachment to PC membranes will be accomplished using commercially available amine-terminated PEG (Nektar, Huntsville, Ala.) and a carbodiimide coupling kit (Polysciences, Warrington, Pa.), following the protocol described by Murthy et al.8 The advantage of this approach is that the same protocol (with minor adjustments for stoichiometry) can be used for the attachment of GAG peptides to the membranes.

The substrate is a material that serves to capture and optionally to provide structure or alignment to the polymer structures. In certain embodiments, assembly of monomers to polymers occurs on the surface of the substrate. In other embodiments, assembly takes place within the microcolumn, and completed polymer is eluted from or drawn out of the microcolumn at the elution end. The substrate can be a planar structure, or it can have other geometries. Suitable substrate materials include glass, polyvinyl alcohol gel, polycarbonate membrane, polyester membrane, dialysis membrane, and silicon. The substrate can also serve as an attachment point for the polymer, and optionally can possess either physical or chemical binding sites for the polymer which bind it to the substrate. The polymer can be either covalently or non-covalently bound to the substrate. The substrate can optionally be bathed in a solution, or it can merely accept solution eluting from the microcolumn. The substrate can be a solid structure, or it can include an interior space. In certain embodiments, the substrate contains or is made of dialysis membrane that encloses a solution, which optionally contains an osmicant for use in transporting or concentrating collagen monomer solution.

The process of "printing" on a substrate using a polymer printhead refers to either deposition of polymer strands or fibrils on a surface of the substrate or to deposition of monomer solution on a surface of the substrate for subsequent assembly to form polymer. The deposition preferably results in a non-random pattern or alignment of polymer on the substrate. Preferred are parallel linear patterns of polymer strands or fibrils. Printing of polymer on a substrate can be performed sequentially, such that multiple layers or other three-dimensional structures are formed on the surface of the substrate.

In some embodiments the substrate possesses either binding sites or structures that assist in controlling the alignment of polymers printed on the substrate. Such binding sites can be randomly distributed, but preferably are arranged in a manner consistent with the desired pattern of polymer strands.

To add polymer binding proteins to a substrate, the substrate can be chemically derivatized so as to react with an added protein that binds the desired polymer. For the case of a substrate prepared from a silicon wafer, each piece of 3 cm×1 cm$^{-1}$ wafer is placed into a 20 mL screw cap vial and then immersed twice in carbonate buffer for 6 minutes each. The wafer piece is then immersed in phosphate buffer for 6 min; this step is repeated three times. Next, the vial is filled with 6.25 mL of phosphate buffer and 6 mL of a 2% carbodiimide solution in phosphate buffer. This mixture is then stirred for 4 hours at room temperature. The wafer piece is then immersed in phosphate buffer for 6 min; this step is again repeated three times. The wafer is then placed in borate buffer and approximately 4 mg of peptide is added. This mixture is gently mixed overnight (about 14 h) at room temperature. Following this step, the wafer is removed and immersed in borate buffer once again and 500 uL of methanolamine is added (to block untreated carboxyl groups). This mixture is stirred for 30 min. The wafer is then immersed in borate buffer for 6 min; this step is repeated once. The wafer is then allowed to dry in air.

The solution bathing the substrate receiving surface can contain any of the substances listed above (see, e.g., monomer solution reservoir) but will preferably contain neutralized phosphate buffered saline. In the case of the delivery of procollagen, the receiving solution will contain C- and N-terminal propeptidases. The receiving solution may also contain collagen cross-linking agents such as lysyl oxidase or glutaraldehyde. Further, the receiving solution can also contain hydroxyapatite to promote calcification of the collagen network produced.

Embodiments that employ cholesteric assembly of collagen fibrils require the use of an osmicant solution in the substrate. The osmicant solution is designed to draw collagen in high concentration from the delivery system onto the receiving substrate via osmotic pressure. The osmicant in the osmicant solution can be any substance that generates a significant osmotic pressure, as the osmotic pressure of the osmicant solution is typically greater than the osmotic pressure of the monomer solution or other solutions sent through the microcolumn. The osmicant is preferably biocompatible. Examples of suitable osmicants include polyethylene glycol (e.g., a 0.1-50% wt/vol solution, e.g., an aqueous buffer such as phosphate buffered saline), a proteoglycan, or a glycosaminoglycan such as hyaluronic acid or chondroitin sulfate.

Temperature-Dependent Self-Assembly

The nanoloom system is a moving system that provides a source of collagen monomers to a location where they are concentrated or confined (e.g., into the pores of a membrane or in a tight space under a porous membrane) such that when the monomers are induced to form fibrils, the local organization of the resulting collagen network is controlled either by the confinement or by cholesteric effects.

Induction of fibrillogenesis in the confined space can be provided by contacting the monomers with enzymes that cleave the propeptides (in the case of procollagen) or by locally causing a suitable increase in the temperature (in the case of extracted collagen, which does not have propeptides), optionally accompanied by a suitable increase in pH. The parameters for controlling the in vitro assembly of collagen and procollagen are well known.

The function of a nanoreactor is similar to that of a cell surface crypt. Collagen monomers are transported from a cold reservoir to the reaction zone (where the pH or temperature, or both, attain critical values) by reputation with or without assistance from electrophoresis or pressure drop. Collagen is prevented from self-assembling prematurely by maintaining steep pH and/or temperature gradients in the channel leading up to the reaction zone. To ensure that the fibril has adequate residence time to assemble, a compliant, permeable substrate (e.g., a gel) can be pressed against the channel opening with a small force. To facilitate removal of the formed fibril from the channel and to induce alignment, the substrate (or the nanoloom) can be translated at a velocity selected to match the rate of transport of fibrils up the channel. Adhesion of collagen to the substrate can be established through collagen binding sites on the substrate.

Figure 9:
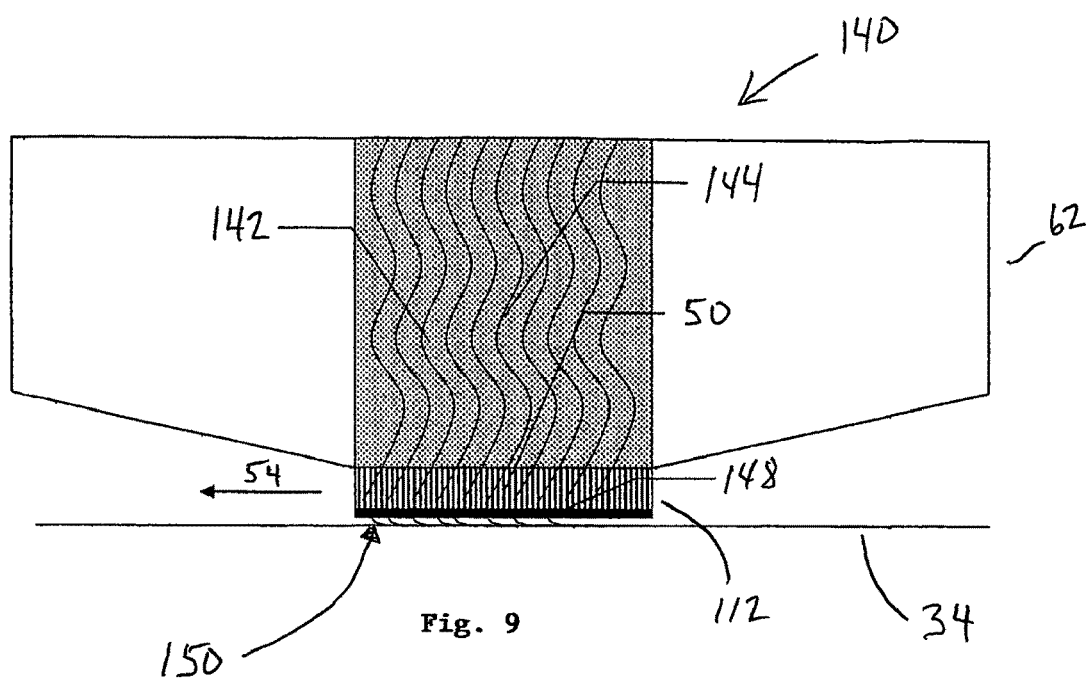
FIG. 9 is a schematic view showing temperature-dependent collagen fibril deposition using optical temperature control of microcolumns according to a method of the invention.
Figure 10:
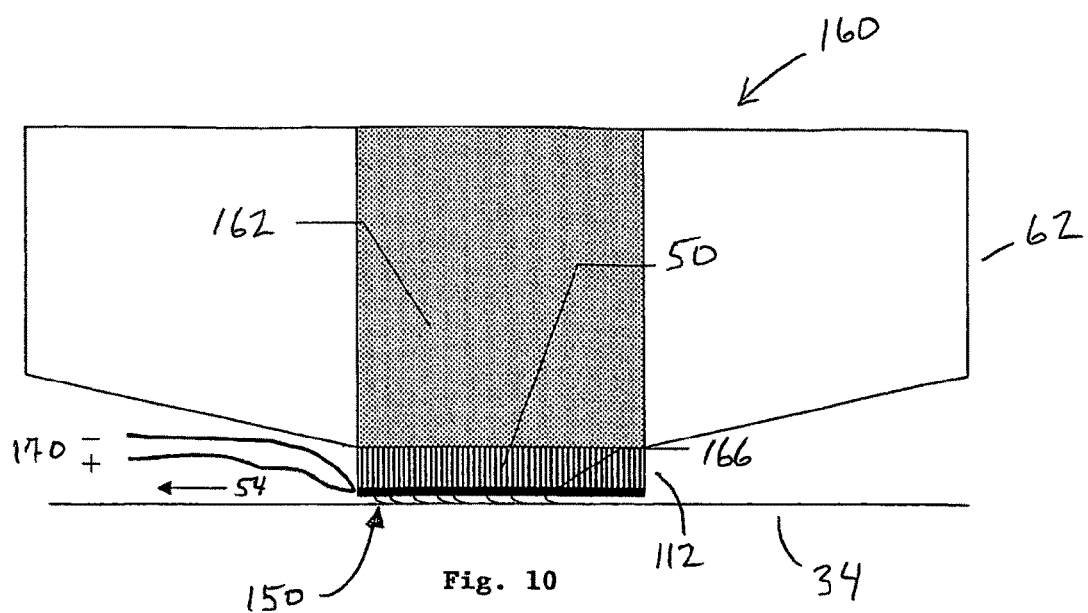
FIG. 10 is a schematic view showing temperature-dependent collagen fibril deposition using electrical resistive heating temperature control of the microcolumns.

Two embodiments of temperature-dependent self-assembly of monomers within a microcolumn array are depicted schematically in FIGS. 9 and 10. These embodiments differ in the temperature control system used to warm the elution end of the microcolumn array, as discussed further below. In either case, various further embodiments exist which relate to the assembly of different polymers. Further discussion is focused on temperature-dependent assembly of extracted collagen.

FIG. 9 shows an embodiment 140 of temperature-dependent assembly process of extracted collagen using light-driven temperature control. Collagen fibrils form in the pores of the membrane 112 and are subsequently drawn out as the printhead 62 moves over the surface of the substrate 34 with velocity 54 as the collagen fibrils 150 are printed. The printhead contains a reservoir with cold monomeric collagen solution 142, which is transparent to the optical radiation 144 used to heat a light absorptive coating 148 deposited on the face of the membrane at the elution side, which creates a temperature gradient 50 within the pores. This is analogous to the fibropositor mechanism that is believed to exist, for example, in tendon. The surface of the track-etched membrane is coated on the collagen fibril elution side with carbon black (graphite) or some other material that will absorb radiation at wavelengths that will not heat either the collagen or the remaining part of the membrane. In this embodiment, the nanoloom printhead is constructed such that radiation can be coupled into the system.

FIG. 10 shows an embodiment 160 of temperature-dependent polymer assembly in which localized heating of the collagen solution is provided by coating the track-etched membrane with a thin film heating element 166. The element is heated by applying current from a power source 170 to the heater. Collagen will polymerize in the vicinity of the heater which is located on the membrane surface. Other localized heating schemes can be used, including magnetic induction heating in a thin film on the membrane or to a series of bound particles on the membrane surface. The collagen monomer solution 162 in the printhead reservoir is cold, but in this embodiment is not required to be transparent to any particular optical radiation. As in the embodiment described in FIG. 9, localized heating of the elution face of the membrane results in a temperature gradient 50 within the pores, thereby driving assembly of collagen fibrils within the pores.

Enzyme-Dependent Self Assembly

According to a widely accepted view of collagen synthesis in vivo, collagen monomers are released at the bottom of an invagination (surface crypt or fibropositor) in the cell membrane where they are prepared for assembly by propeptidase cleavage of the N- and C-terminal propeptides. In the confines of the surface crypt, the collagen fibril is constructed and then vectorially discharged into the extracellular space.

Conditions for enzyme-dependent assembly are described in Miyahara et al., 1984. Enzyme-dependent self-assembly ensues following cleavage of one or more propeptide segments from a monomer precursor protein. In order to practice this method, one or more propeptidase enzymes, or other suitable enzymes that are capable of cleaving a propeptide, are included in the solution bathing the substrate, or are attached to or embedded within the substrate. Cold monomer solution is deposited onto the substrate from a microcolumn or microcolumn array. Conditions within the microcolumn are chosen (e.g., low temperature and/or low pH) to prevent self-assembly. Warm temperatures may be used if the presence of a propeptide in the monomer precursor prevents assembly. Once appropriate cleavage of propeptide occurs on the substrate, assembly occurs spontaneously, or optionally after warming the solution.

Cholesteric Assembly of Collagen Fibrils

The above collagen delivery mechanisms and temperature control embodiments are also applicable to the methods by which collagen is organized not within the surface crypts, but by cholesteric confinement in the space 206 under the track-etched membrane. The same method of heating applies but the collagen concentration under the membrane is driven up by convective transport and entrapment against a dialysis membrane which is acting as a substrate.

Figure 11:
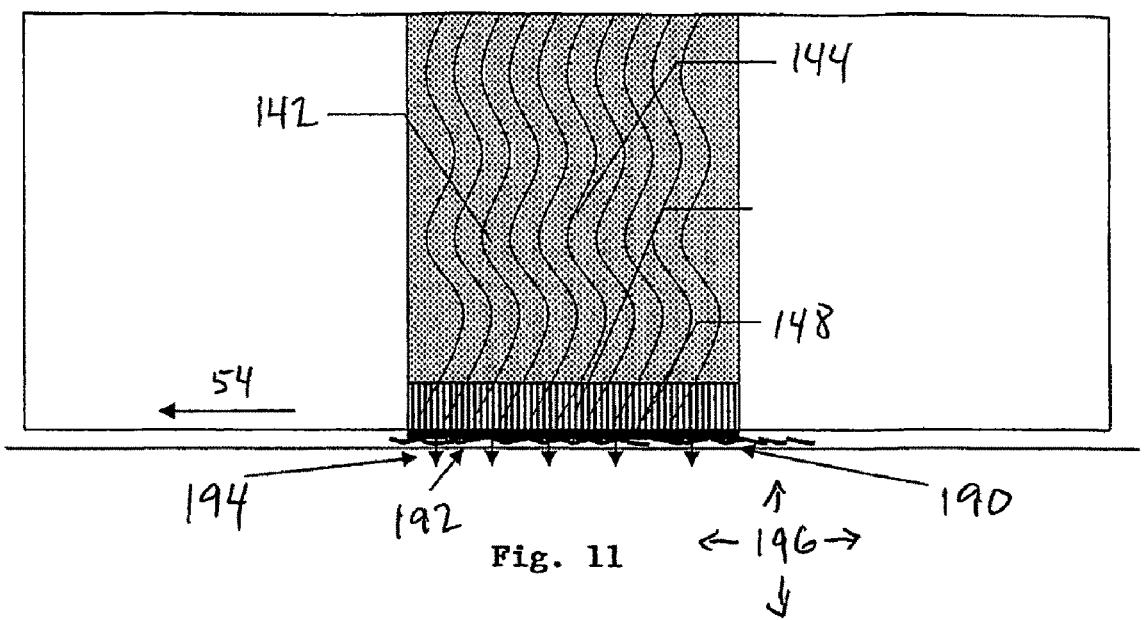
FIG. 11 is a schematic view showing cholesteric collagen fibril deposition using optical temperature control of the microcolumns.
Figure 12:
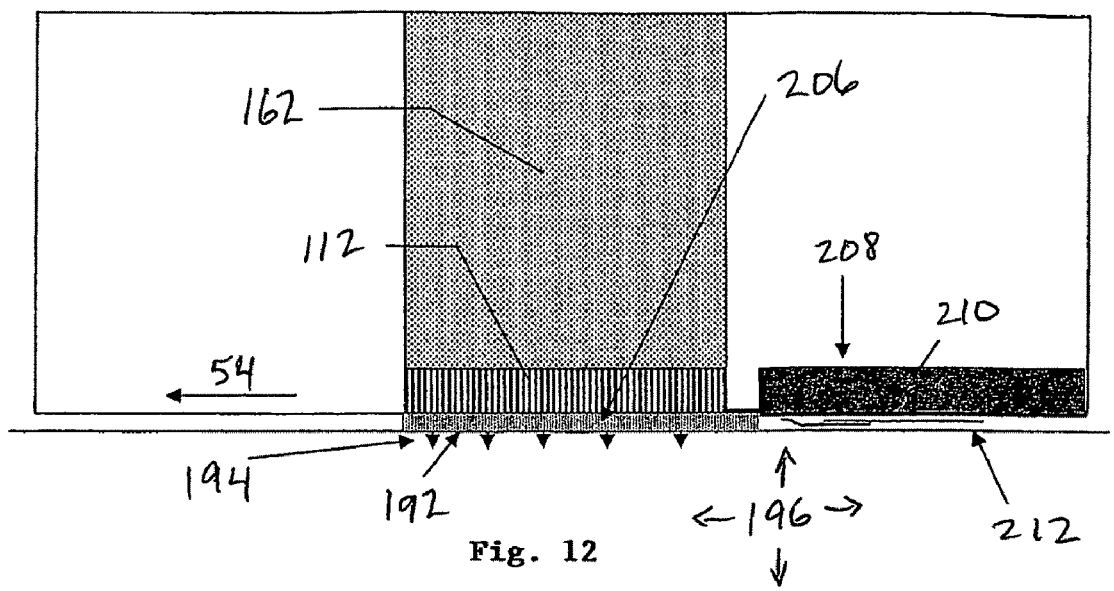
FIG. 12 is a schematic view showing cholesteric collagen fibril deposition using a patterned heating block.

Two embodiments of cholesteric assembly of collagen are depicted in FIGS. 11 and 12. The embodiment shown in FIG. 11 employs light-driven warming of an absorptive layer 148 deposited at the elution face of the microcolumn array (membrane), which warms the fluid space between the printhead and the substrate. In the embodiment shown in FIG. 12, warming is supplied through a temperature-controlled heating block 208 that optionally includes a patterned surface 210, producing a zone of collagen fibril assembly 212 beneath the block. In both embodiments, collagen is concentrated osmotically under the membrane and induced to form fibrils on the substrate, optionally under a patterned surface to control alignment at the trailing edge of the nanoloom printerhead. Fibrillogenesis induction is thermal for extracted collagen monomers but could be enzymatic for procollagen. The patterned surface may be produced on any material that can accept nanoscale topographic linear patterns in the range of 20-500 nm periodicity. Preferably, the patterned surface will be collagen-rejecting so it will not bind to fibrils. This can be accomplished by fixing molecules such as PEG to the surface which has been extensively reviewed in the open literature for a number of materials. One suitable choice for a patterned trailing surface is silicon. Silicon has good heat conductivity, can be patterned on the nanoscale and can be functionalized with PEG molecules to prevent collagen attachment.

In order to achieve cholesteric collagen assembly, the collagen monomer concentration is initially in the range of 0.1-10.0 mg/ml (reservoir and microcolumn), and the concentration is raised by removal of water through osmotic forces to a final monomer concentration in the range of 5.0-1000 mg/ml in the fibril forming space 190 or 212. Collagen final concentration can be controlled by controlling the osmotic pressure gradient (i.e., adjusting the concentration of osmicant in the osmicant solution 196, which produces a flow of water 194 across a substrate comprising dialysis membrane 192) and by printer head speed. The suitable range of osmotic pressure difference between the monomer solution exuded onto the substrate and the osmicant solution is 5-1000 PSI.

It is also possible to generate organized fibrillar collagen by cholesteric means if collagen monomer solution is first concentrated (5.0-1000 mg/ml) in a layer on top of a dialysis membrane which rests on a solution with high osmolarity (e.g., PEG at 1%-50% wt/vol). Subsequent to concentration, the layer of cholesteric collagen monomers are then contacted with a patterned, collagen-rejecting surface (e.g., PEGylated silicone with linear features as described above) for a period of time. To polymerize the aligned collagen monomers, the patterned substrate or entire system is heated to 37° C. Following fibrillogenesis, the patterned substrate is removed and the process is repeated on top of the previously polymerized collagen to produce a 3-dimensional stack of organized collagenous matrix. In this manner, it is possible to use the patterned substrate to determine the direction of alignment of collagen fibrils in each layer made by cholesteric assembly.

Manufacture of Tissue Products

Developing tissues that establish a high degree of organization possess a high ratio of cell volume to matrix volume. For example, this is a characteristic of a developing cornea in vivo. Later in life, damaged tissue cannot get very organized and scars result. Even under ideal conditions, damaged tissue takes very long periods of time to resolve. Therefore, using a degradable scaffolding and a low cell density probably will not yield an organized tissue. Thus far, there are no engineered, highly-organized tissues that are load bearing and clinically viable. However, a polymer printhead can be used to deliver collagen from a concentrated source to a confined space, leading to the production of highly aligned collagen fibrils. The local alignment of the collagen is driven by cholesteric forces, while the direction of the collagen fibrils can be controlled by surface patterning on the membrane. This concept is similar to how cells in developing tissues control collagen alignment.

The family of fibrillar collagens are arguably the most important structural molecules found in animals. In humans, they provide the template for bones prior to mineralization, a reinforcing network of constraining fibrils in cartilage and are the principle load-bearing molecules in tendons and ligament. There are many other tissues that contain collagen, but the cornea is the most highly-organized collagenous extracellular matrix (ECMs) in higher animals.

In fabricating artificial tissues and tissue templates, minerals such as hydroxyapatite or accessory proteins that bind or organize polymer strands can be employed. Further, the use of chemical cross-linkers can add strength to the product and enhance load bearing capacity. Examples of structures that can be formed include ligament, tendon, cornea, and annulus fibrosis.

A useful adjunct to fabricating polymer scaffolds is the addition of cells to such structures, thereby establishing a living tissue and aiding in the further development and maintenance of the tissue. Thus cells can be added to the polymer products of the invention at any stage of production, including adding cells to the substrate prior to polymer printing, at any time during polymer printing, or after polymer printing. When making three-dimensional structures, the addition of cells during the fabrication of intermediate layers can be useful to incorporate cells into the structure. Any type of mammalian cells can be added; however fibroblasts, particularly human fibroblasts, are preferred. Other tissue-specific cell types (e.g., chondrocytes, osteoblasts) can be useful when preparing tissue constructs specifically designed for incorporation into a particular tissue.

Temperature Control Systems

Figure 13:
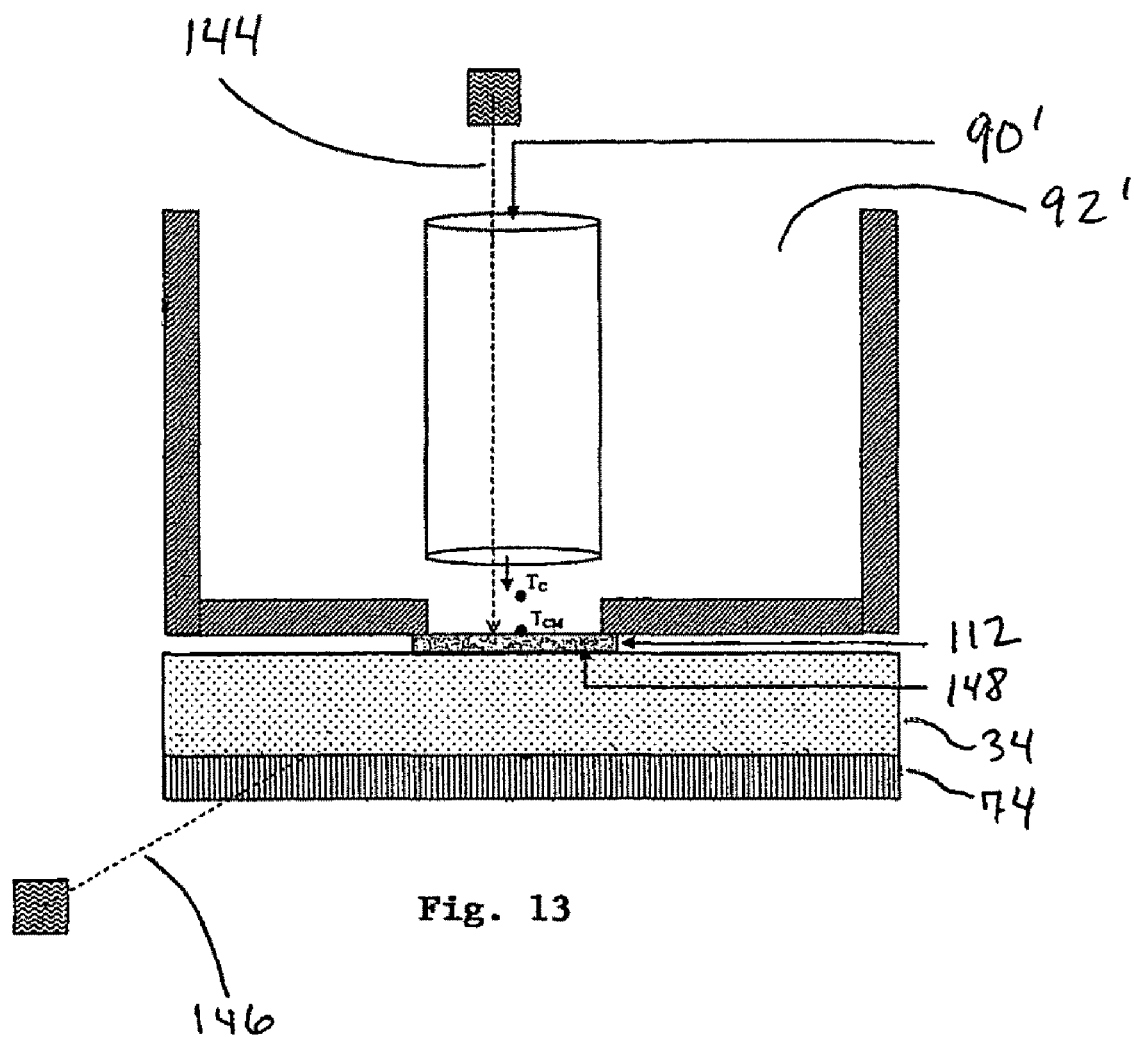
FIG. 13 is a schematic view showing a system for optical heating of a microcolumn membrane apposed to a thermally controlled substrate.

The thermal transport through the system shown in FIG. 13 is controlled to maintain the temperature at the interface of the monomer solution and a biomimetic membrane (e.g., a track-etched membrane serving as an array of microcolumns), $T_{cm}$, in the range of 2 to 4° C., (preferred value 4° C.) and the temperature at the membrane-collection substrate (BMCS) interface, $T_{sm}$, in the range of 25 to 37° C. (preferred value 37° C.). The thermal transport in the porous biomimetic membrane is a parallel combination of conduction and convective transport carried by the collagen flow. The temperature field through the membrane is determined from the differential energy balance.

$$T = C_0\left(\frac{k}{\rho c V_c}\right)\exp\left[\left(\frac{\rho c V_c}{k}\right)z\right] + C_1 \quad (1)$$

where $$C_0 = \frac{T_{cm} - T_{sm}}{\left(\frac{k}{\rho c V_c}\right)\left[1 - \exp\left[\left(\frac{\rho c V_c}{k}\right)L_m\right]\right]}$$

$$C_1 = Tcm - C_0\left(\frac{k}{\rho c V_c}\right)$$

$L_m$=membrane thickness,
$V_c$=collagen velocity within the membrane,
ρ=density of collagen flow,
c=specific of collagen,
k=thermal conductivity of the membrane, and
z=distance through the collagen.
The heat flux through the membrane at the BMCS interface is $$q'' = C_0 \exp\left[\left(\frac{\rho c V_c}{k}\right) L_m\right] \quad (2)$$

The temperature set points, $T_{cm}$ and $T_{sm}$, are achieved in practice by several different means. The temperature $T_{cm}$ is maintained at the preferred 4° C. by adjusting both the flow rate and temperature, $T_c$, of collagen flow from the monomer reservoir. The input temperature can vary in the range of 0 to 4° C. The convective heat transfer mechanism is an impinging jet flow type and is controlled by varying the diameter and distance of the tube end from the membrane (see FIG. 13). The flow rate is controlled by adjusting the pump speed and pressure difference in the system.

One method of maintaining the BMCS interface temperature is to conductively add heat from the thermal control base. The energy removed by the flow of collagen from the fibrils laid down on the substrate is negligibly small because of the large increase in its flow area as compared to that in the printhead. This heat flow path is dominated by conduction, low peclet number, and is described as a thermal circuit analogy. The thermal control base temperature, $T_B$, required to maintain the temperature at the BMCS interface is calculated using this model and the results of Eq. 2.

$$T_B = q''(R_{es}) + T_{sm} \quad (3)$$

where
Rcs=thermal resistance of the collagen collection substrate=$L_S/k_s$,
$L_S$=collagen collection substrate thickness, and
$k_s$=substrate's thermal conductivity.

Figure 14:
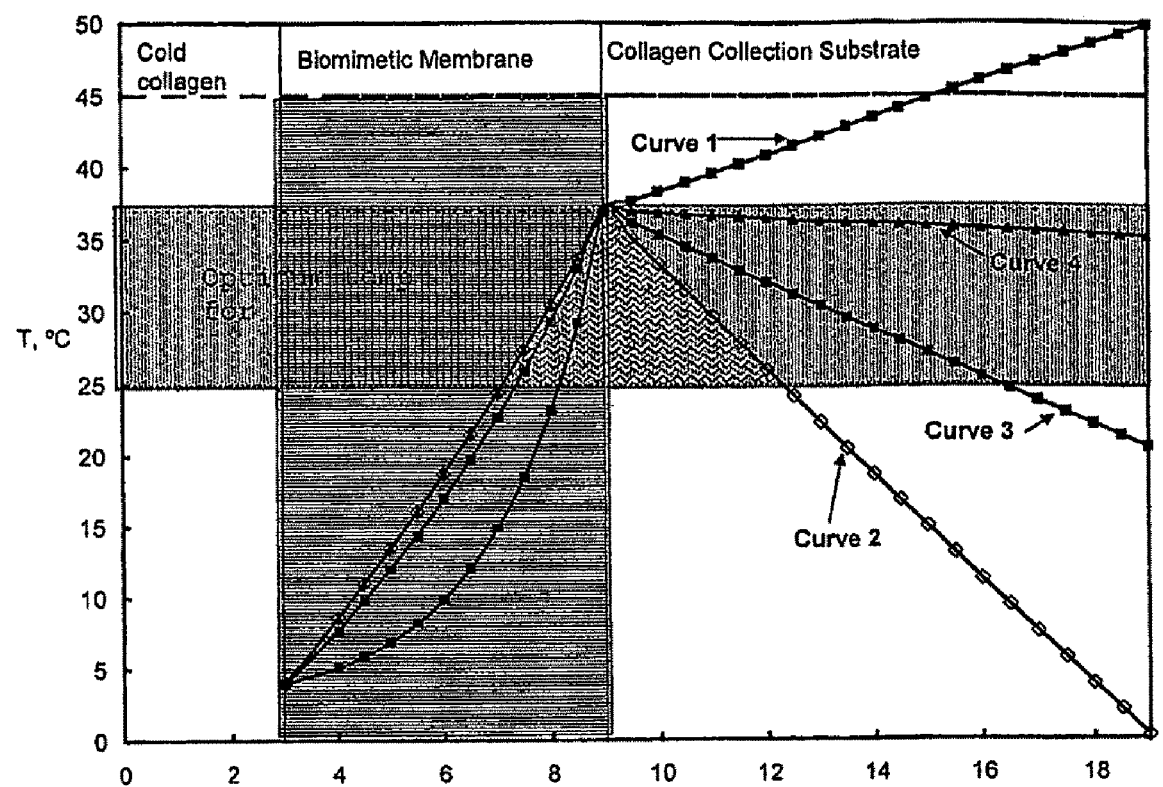
FIG. 14 is a theoretical depiction of temperature gradients across a microcolumn apposed to a substrate.

The temperature field in the collagen collection substrate is linear. Using the above formulation the temperature field in the membrane and the collagen collection substrate for the representative conditions discussed above is calculated and summarized in FIG. 14. These calculations are based on values of a membrane thickness of 6 μm and a substrate thickness of 10 μm. Preferred values of membrane thickness range from 6 to 15 μm and of the collection substrate range from 5 to 15 μm or larger (there is in principle no upper limit to the thickness of the substrate, except due to the constraints imposed by temperature control). Curve 1 in FIG. 14 illustrates the expected temperature field for this type of thermal control when the velocity of the collagen is 0.07 m/s through the membrane. The thermal control base temperature is required to be maintained at 50° C. This temperature could be maintained using electrical heating provided by cartridge or foil heaters or by circulating temperature controlled water through channels in the plates. There are many means of providing this temperature-heat flow combination which are well known. Curve 1 demonstrates that there is a region near the BMCS interface which is below 45° C., the denaturing temperature of collagen, and 25° C. the minimum temperature for collagen to organize.

A second method to maintain the appropriate conditions is to provide a surface heating mechanism to the BCMS interface. Means for providing this surface heating mechanism are discussed below. In this case the boundary condition at this interface becomes:

$$q'' = q_{substrate} - Q_{surf} \quad (4)$$

where
$q_{substrate}$=heat flux through the substrate (1/$R_{cs}$) ($T_{sm}-T_B$)
and
$Q_{surf}$=surface heat flux provided by specified mechanism.
The temperature of the thermal control base is determined by combining Eq. 2 through 4 and is the same form as Eq. 3.

The temperature through the collagen collection substrate is again determined using Eq. 3 with the thermal control base temperature calculated using Eq. 4 for the heat flux. The temperature field in the proposed device for this type of thermal control system is shown in FIG. 14 with Curves 2 through 4. The geometry used in these simulations is the same as for curve 1. The collagen velocity and surface heat flux input for curves 2 to 4 are as follows:

| curve | Velocity(m/s) | Surface heat flux(w/m2) |
|---|---|---|
| 2 | 0.01 | 7.5 ($10^6$) |
| 3 | 0.02 | 5 ($10^6$) |
| 4 | 0.01 | 5 ($10^6$) |

The results for curve 2 clearly demonstrate the preferred sharp temperature spike in the region of the BCMS interface. However, the results for curves 3 and 4 would also lead to an operating device. The effect of controlling the collagen velocity in the membrane is illustrated by comparing curves 3 and 4 which are at the same surface heating level and at different velocities.

The results shown in FIG. 14 indicate that the thermal control base is able to heat or cool this region of the device. This can be accomplished in any number of practical means. Using Peltier cooling/heating devices or the use of a cold plate are two examples of many potential means of maintaining a thermally controlled surface.

The surface heating mechanism can also be provided by many different means. One preferred method consists of using a radiation source such as a laser or filter light source to provide the heating. In this case an absorptive film coating would be laid down as shown in FIG. 13 that would absorb light in a wavelength spectrum. The wavelength spectrum used is chosen such that the polymer (e.g., collagen) is highly transparent to it. One combination would be to use a Helium-Neon laser at 534 nm with a carbon black coating on the membrane. The collagen is transparent at this wavelength and the film coated membrane surface is highly absorptive to the laser light. A 20 watt laser provides sufficient power to achieve the conditions of curve 2 in FIG. 14. Other types of light sources include any laser in the visible spectrum, a $CO_2$ laser or Xeon light sources. Using the laser pulsed at high frequency to reduce the penetration depth of the heated region provides further control options to make the temperature spike at the BCMS interface sharper. The radiation source can be mounted either above or below as shown in FIG. 13 and the incident radiation can be transmitted to the device through a fiber optic system.

A thin polymer layer containing sufficient carbon black can be added to the elution side of a track etch membrane so as to be able to locally heat this layer with laser radiation, as well as to maintain tight spatial control of the temperature. Carbon black polymers for coating compositions are described, for example, in U.S. Pat. No. 4,880,857 as well as in Doleman et al., 1998. A specific polymer-carbon black composite can be prepared and spin-coated onto the surface of a polymer membrane, providing a thin layer that will be thermally responsive to laser radiation with minimal effect on the bulk polymer that this composite is attached to. Poly(vinyl acetate) and poly (methyl methacrylate) can be used as the polymer systems. These polymer systems can be used independently or as co-polymer blends, depending upon the specific needs of the system. PVA/PMMA mixtures with mol fractions of PVA (by monomer) spanning the compositional range can be fabricated. For example, a solution can be prepared containing 20 mL of tetrohydrofuran (as solvent), 200 mg total dissolved polymer, and approximately 100 mg of suspended carbon black. The amount of carbon black can be varied so as to vary the absorptive potential of the polymer composite. The polymer-carbon black suspension is then sonicated for 10 minutes to promote good mixing, and is then spin coated at approximately 1000 rpm. Rotational speed can be varied to control the thickness of the final composite layer. The composite is then dried at ambient conditions for approximately 12 hours. The carbon black loading can be varied to tune the degree of heating by the laser, and the laser wavelength should be chosen so as to minimize the heating of any surrounding materials.

Alternatively, a surface layer of light absorbing material can be added to a track-etched membrane using a chemical vapor deposition technique. For example, asymmetrical magnetron sputtering of a graphite target can be used. The membrane should be about room temperature and should be cleaned in situ by ion bombardment. Alternatively, for better adhesion, sputter ion plating can be used. In that case, RF power is applied to the membrane.

Optical heating also can be used to warm the substrate. For example, if the substrate is coated on a surface with a light absorptive material, then illumination from below (see FIG. 13, 146) can provide local heating of the substrate which is independent of any optical heating of the BMCS interface.

The surface heating can also be provided by other means such as coating the membrane at the BCMS interface with a conductive layer and using electrical and inductive heating devices to provide the surface heating mechanism. Ultrasonic stimulation of the membrane at the BCMS interface is another mechanism of providing this type of surface heating. All coating methods must preserve the membrane porosity.

Another method of providing the thermal control is to construct the membrane as a porous semiconductor device that would allow the use of the Peltier heating and cooling effect. In this embodiment the membrane would be coated with semiconductor films at both the BCMS and FBM interfaces with a semiconductor film that is then coated with a corrosion protective layer. The semiconductor material is chosen and connected in a manner to provide peltier cooling at the FBM interface and peltier heating at the BCMS surface. The heat produced by this device would be removed by conducting through the collagen collection substrate. From a thermal simulation viewpoint this device would appear as the surface heating mechanism model described above.

Pressure Control Systems

A pressure head ($\Delta P$), e.g., 5, 10 or 20 cm/H$_2$O can be applied to the loading end of the microcolumn using a perfusion apparatus. In one embodiment the apparatus includes an injection-only syringe pump (Harvard Apparatus PHD 22/2000, Holliston, Mass.), a pressure transducer (Sager Electronics, Hingham, Mass.), and a computer equipped with PCI data acquisition (National Instruments, Austin, Tex.). The system can work in either pressure or flow control mode. The monomer solution can be delivered from a gastight syringe to ensure bubble-free conditions, and all the fluid lines can be kept chilled in order to prevent premature self-assembly. A peristaltic pump (Watson-Marlow Sci-Q 401U/D, England) can be used to recirculate the fluid in the monomer solution reservoir, preventing depletion or overflow and ensuring thorough mixing. As described by Anderson and Malone (Anderson, et al., 1974), the equation for the flux of solvent across the membrane, $J_v$ (cm/s) is:

$$J_v = L_p[\Delta P_\infty - \sigma_0 \Delta \Pi_\infty] \qquad (5)$$

where the subscript $\infty$ indicates bulk solution conditions on each side of the membrane, $L_p$ is the "hydraulic coefficient" which is specific to each membrane and solvent combination, $\sigma_0$ is the reflection coefficient and $\Delta \Pi$ is the pressure difference at $J_v=0$, which depends on the solute concentration difference. For an ideal solution $\Delta \Pi$ is equal to the product $RT\Delta C\infty$. Here, however, $\Delta \Pi$ should be experimentally determined. $\sigma_0$ is a function of solute and membrane characteristics and does not significantly depend on pressure and concentration. Strictly, Equation 1 is only valid for negligible unstirred layers in the bulk solution adjacent to the membrane. The equation for the flux of solute through the membrane ($J_s$, mg/cm$^2$-s) is:

$$J_s = J_v \hat{C}[1-\sigma_a] + D\Delta C/h \qquad (6)$$

Where $\hat{C}$ (mg/ml) indicates the average concentration in the bulk solution, D (cm$^2$/s) is the diffusion coefficient of collagen through the membrane, h (cm) is the thickness of the membrane and $\Delta C$ is the concentration gradient across the membrane (mg/ml). Combining Equations 1 and 2, and given that data are available for the case $J_v=0$, the remaining transport parameters can be obtained from regression of data obtained in experiments where $\Delta P$ and $\Delta C$ are the experimental variables.

Motion Control Systems

Motion control for the nanoloom can be achieved by a number of means which permit relative motion between the printer head and the printing substrate. For example, FIG. 3 depicts a system where the printing substrate is mounted on an X-Y motion control stage. X-Y motion control can be accomplished by stacking individual linear nanomotion stages, such as the stackable Aerotech ALS130-025, which has 5 nm spatial resolution, a position accuracy of ±1.0 micron and a velocity range from 0-300 mm/sec. The Z-stage is required to lower the printer head onto the printing substrate and can be accomplished by any reasonably high resolution linear motor such as the Aerotech ATS50-25 which has a spatial resolution of 300 nm and the ability to apply a force of up to 5 kg onto the printing surface. The printer substrate motion may also be rotational allowing collagen to be printed in 3-D with cylindrical coordinate control. Such a system could be produced by combining the Aerotech ATS50 with an Aerotech ART50 rotational stage. The printing substrate may also be part of a rotating drum or sphere, such that the printhead is lowered onto and perpendicular to the motion of the drum or sphere.

The following examples are presented to illustrate the advantages of the present invention and to assist one of ordinary skill in making and using the same. These examples are not intended in any way otherwise to limit the scope of the disclosure.

EXAMPLE 1

Use of Nanoloom in Fibropositor Mode with Optical Illumination Heating

Neutralized collagen monomer solution (3.0 mg/ml) in phosphate buffered saline (PBS) is recirculated through the reservoir in the printer head such that it impinges on a plurality of right circular columns which traverse a polycarbonate, track etched membrane which is 6 microns thick containing 80 nm pores at a 20% areal fraction at 4° C. In this way the recirculated solution is not only a source of collagen monomers, it also provides a cooling flow to keep the cold side of the membrane as close to 4° C. as possible. The solution in the reservoir is kept cool by Peltier thermoelectric devices and is recirculated at a flow rate of 0.5 ml/min via a peristaltic pump. To aid in driving the collagen solution across the membrane, the pressure in the reservoir is raised to 1.0 psi by restricting the outlet flow on the low-pressure side of the pump. The exit side of the membrane is in contact with, and moving across, a collagen binding substrate, which also modulates the exit of collagen from the pores. The lateral velocity of the printer head is 1 mm/sec to assure adequate residence time for collagen self-assembly. At a collagen flux of 0.1 mg/min, a printer head velocity of 1 mm/sec leaves a track of collagen that is 2 mm wide and has a mass of $1.6 \times 10^{-3}$ mg/mm. To facilitate assembly of the collagen monomers at the membrane exit and to prevent premature assembly of the collagen on the reservoir side of the membrane, a highly-localized heating system ensures that the temperature at the membrane outlet reaches 37° C. The system comprises an optical laser which is designed to deliver energy to the exit side of the printer head membrane. The coupling of the laser energy to the membrane is accomplished by means of a layer of graphite (carbon black) which is plated onto the polycarbonate membrane via asymmetrical magnetron sputtering. The laser energy source is a helium-neon gas laser with a wavelength of 632.8 nm which is minimally absorbed by the collagen monomer and the polycarbonate part of the membrane. The carbon coating absorbs the laser energy causing a local temperature rise. The amount of power required to heat the membrane is 5 mW. The substrate onto which the collagen is printed (treated polycarbonate membrane) prevents the collagen from escaping the printer head membrane columns but also promotes collagen adhesion to its surface. The printing substrate is treated with carbodiimide followed by borate buffer treatment. The printing substrate is immersed in a thin layer of PBS, backed by polyvinyl alcohol gel and temperature controlled to 4° C.

EXAMPLE 2

Use of Nanoloom in Cholesteric Mode with Trailing Edge Patterning and Heating Neutralized collagen monomer solution (3.0 mg/ml) in PBS is recirculated through the reservoir in the printer head such that it impinges on a plurality of right circular columns which traverse a polycarbonate, track etched membrane which is 6 microns thick containing 80 nm pores at a 20% areal fraction at 4° C. The solution in the reservoir is kept cool by Peltier thermoelectric devices and is recirculated at a flow rate of 0.5 ml/min via a peristaltic pump. To aid in the driving of the collagen solution across the membrane, the pressure in the reservoir is raised to 1.0 psi by restricting the outlet flow on the low-pressure side of the pump. Flow across the membrane is modulated also by the generation of an osmotic pressure sink below the printer head. The lateral velocity of the printer head across the substrate is 1 mm/sec) to assure adequate time for collagen to concentrate to a cholesteric level of about (50 mg/ml) via compaction under the printer head assembly. At a collagen flux of 1 mg/min, a printer head velocity of 1 mm/sec leaves a track of collagen that is 2 mm wide and has a mass of $1.6 \times 10^{-2}$ mg/mm. To prevent the assembly of the collagen monomers at the membrane exit, the substrate and the membrane are kept at 4° C. Thus there is a region- of highly concentrated collagen under the printer head. To facilitate organized assembly, a heating block with a patterned surface (silicon wafer) comprising a linear pattern of 50 nm troughs 50 nm deep and spaced at 100 nm center-to-center is positioned at the trailing edge of the printer head and is maintained at 37° C. The collagen monomers (at high concentration), are passed over by the patterned trailing surface and organized according to the pattern; heating then drives fibrillogenesis while the collagen monomers are organized. The space between the patterned surface and the collagen is dictated by the conformity of the substrate membrane and the concentration of the collagen. In this system, the substrate onto which the collagen is printed is a dialysis membrane (3000 mwco) in the first pass and subsequently is assembled collagen from a previous pass. The osmotic pressure, drives the concentration of the collagen is generated by the presence of a concentrated osmicant (25% wt/vol PEG) that is under the dialysis membrane.

REFERENCES

Anderson et al., "Mechanism of Osmotic Flow in Porous Membranes", *Biophysical Journal*, Vol. 14, pp. 957-982 (1974).

Braithwaite et al., "Layered Aligned Polymer Structures and Methods of Making Same", US Publication Number 2003014618.

Doleman, et al., "Use of Compatible Polymer Blends to Fabricate Arrays of Carbon Black-Polymer Composite Vapor Detectors", *Analytical Chemistry*, Vol. 70, No. 13, pp. 2560-2564 (1998).

Guido et al., "Methodology for the Systematic and Quantitative Study of Cell Contact Guidance in Oriented Collagen Gels", *Journal of Cell Science*, Vol. 105, pp. 317-331 (1993).

Holmberg et al., "Immobilization of Proteins Via PEG Chains", *Poly(Ethylene Glycol)Chemistry: Biotechnical and Biomedical Applications*, (Harris, J. M., Ed.), Plenum Press, New York, pp. 303 (1992).

Lee, J. H. et al., "Blood Compatibility of Polyethylene Oxide Surfaces", *Progress in Polymer Science*, Vol. 20, pp. 1043-1079 (1995).

Lee, S. W. et al., "Protein-resistant Surfaces Derived From Oligo(Ethylene Glycol)-Terminated. Alkyltrichlorosilanes", *Biomaterials*, Vol. 19, pp. 1669-1675 (1998).

Malmsten et al., "Effect of Chain Density on Inhibition of Protein Adsorption by Poly(Ethylene Glycol) Based Coatings", *Journal of Colloid and Interface Science*, Vol. 202, pp. 507-517 (1998).

Miyahara et al., "Formation of Collagen Fibrils By Enzymatic Cleavage of Precursors of Type I Collagen In Vitro", *Journal of Biological Chemistry*, Vol. 259, No. 15, pp. 9891-9898 (1984).

Murthy et al., "Peptide Attachment to Vapor Deposited Polymeric Thin Films", *Langmuir*, Vol. 20, pp. 4774-4776 (2004).

Prime et al., "Self-Assembled Organic Monolayers-Model Systems for Studying Adsorption of Proteins at Surfaces", *Science*, Vol. 252, pp. 1164-1167 (1991).

Prime et al., "Adsorption of Proteins Onto Surfaces Containing End-Attached Oligo (Ethylene Oxide)-a Model System Using Self-Assembled Monolayers", Journal of the *American Chemical Society*, Vol. 115, pp. 10714-10721 (1993).

Sofia et al., "Poly(Ethylene Glycol): Chemistry and Biological Applications", *American Chemical Society* (Zalipsky, S., Ed.) Washington, D.C., Vol. 680, pp. 342-360 (1997).

Wilson et al., "Surface Organization and Nanopatterning of Collagen by Dip-pen Nanolithography", *PNAS*, Vol. 24, pp. 13360-13364 (2001)

Other embodiments of the invention will be apparent to those skilled in the art from a consideration of this specification or practice of the invention disclosed herein. It is intended that the specification and the examples be considered as exemplary only, with the true scope and spirit of the invention being indicated by the following claims.

What is claimed is:

1. A system for the patterned deposition of a polymer by self-assembly, the system comprising:
   a polymer printhead comprising
      a monomer solution reservoir and
      a microcolumn fluidically coupled at a loading end to the reservoir, said microcolumn also having an elution end;
   a temperature controller for regulating temperature within the microcolumn, wherein the microcolumn temperature is regulated either as a constant temperature throughout the microcolumn or as a gradient of increasing temperature from the loading end to the elution end of the microcolumn;
   a substrate mounted in apposition to the elution end of the microcolumn and movable in a plane orthogonal to the axis of the microcolumn for deposition of a polymer of said monomer onto a surface of the substrate apposed to the microcolumn; and
   a movable stage for relative X-Y positioning of the substrate and the polymer printhead.

2. The system of claim 1, wherein the movable stage further allows positioning of the substrate and the polymer printhead in a Z direction.

3. A system for the patterned deposition of a polymer by self-assembly, the system comprising:
   a polymer printhead comprising
      a monomer solution reservoir and
      a plurality of microcolumns each fluidically coupled at a loading end to the reservoir, said microcolumns also having an elution end, wherein, each microcolumn is fluidically attached to a common reservoir and each microcolumn is apposed to a common substrate;
   a temperature controller for regulating temperature within the microcolumns, wherein the temperature of the microcolumns is regulated either as a constant temperature throughout the microcolumns or as a gradient of increasing temperature from the loading end to the elution end of the microcolumns; and
   a substrate mounted in apposition to the elution end of the microcolumns and movable in a plane orthogonal to the axis of. the microcolumns for de osition of a polymer of said monomer onto a surface of the substrate apposed to the microcolumns.

4. The system of claim 3, wherein the microcolumns are pores within a track-etched membrane.

5. The system of claim 3, wherein the microcolumns are located in a membrane and share a common patterned elution surface.

6. The system of claim 5, wherein the membrane is coated with a material that warms the elution end of the microcolumns or the solution eluted from the microcolumns in response to light absorption, electrical resistance heating, or magnetic induction.

7. The system of claim 5, wherein the membrane is chemically derivatized for reducing the binding of the monomer or a polymer of the monomer to the membrane.

8. A system for the patterned deposition of a polymer by self-assembly, the system comprising:
   a polymer printhead comprising
      a monomer solution reservoir and
      a microcolumn fluidically coupled at a loading end to the reservoir, said microcolumn also having an elution end, wherein the length of the microcolumn is in the range of 1-100 microns;
   a temperature controller for regulating temperature within the microcolumn, wherein the microcolumn temperature is regulated either as a constant temperature throughout the microcolumn or as a gradient of increasing temperature from the loading end to the elution end of the microcolumn; and
   a substrate mounted in apposition to the elution end of the microcolumn and movable in a plane orthogonal to the axis of the microcolumn for deposition of a polymer of said monomer onto a surface of the substrate apposed to the microcolumn.

9. A system for the patterned deposition of a polymer by self-assembly, the system comprising:
   a polymer printhead comprising
      a monomer solution reservoir and a microcolumn fluidically coupled at a loading end to the reservoir, said microcolumn also having an elution end, wherein the diameter of the microcolumn is in the range of 5 nm-4 microns;
   a temperature controller for regulating temperature within the microcolumn, wherein the microcolumn temperature is regulated either as a constant temperature throughout the microcolumn or as a gradient of increasing temperature from the loading end to the elution end of the microcolumn; and
   a substrate mounted in apposition to the elution end of the microcolumn and movable in a plane orthogonal to the axis of the microcolumn for deposition of a polymer of said monomer onto a surface of the substrate apposed to the microcolumn.

10. A system for the patterned deposition of a polymer by self-assembly, the system comprising:
    a polymer printhead comprising
       a monomer solution reservoir and
       a microcolumn fluidically coupled at a loading end to the reservoir, said microcolumn also having an elution end, wherein an interior surface of the microcolumn is chemically derivatized to reduce the binding of the monomer, or a polymer of the monomer, to the microcolumn;
    a temperature controller for regulating temperature within the microcolumn, wherein the microcolumn temperature is regulated either as a constant temperature throughout the microcolumn or as a gradient of increasing temperature from the loading end to the elution end of the microcolumn; and
    a substrate mounted in apposition to the elution end of the microcolumn and movable in a plane orthogonal to the axis of the microcolumn for deposition of a polymer of said monomer onto a surface of the substrate apposed to the microcolumn.

11. A system for the patterned deposition of a polymer by self-assembly, the system comprising:
    a polymer printhead comprising
       a monomer solution reservoir and
       a microcolumn fluidically coupled at a loading end to the reservoir, said microcolumn also having an elution end;

a temperature controller for regulating temperature within the microcolumn, wherein the microcolumn temperature is regulated either as a constant temperature throughout the microcolumn or as a gradient of increasing temperature from the loading end to the elution end of the microcolumn, wherein the temperature controller provides a gradient across the microcolumn from 0° C.-15° C. at the loading end to 25° C.-50° C. at the elution end; and a substrate mounted in apposition to the elution end of the microcolumn and movable in a plane orthogonal to the axis of the microcolumn for deposition of a polymer of said monomer onto a surface of the substrate apposed to the microcolumn.

12. A system for the patterned deposition of a polymer by self-assembly, the system comprising:

a polymer printhead comprising
a monomer solution reservoir and
a microcolumn fluidically coupled at a loading end to the reservoir, said microcolumn also having an elution end;

a temperature controller for regulating temperature within the microcolumn, wherein the microcolumn temperature is regulated either as a constant temperature throughout the microcolumn or as a gradient of increasing temperature from the loading end to the elution end of the microcolumn;

a substrate mounted in apposition to the elution end of the microcolumn and movable in a plane orthogonal to the axis of the microcolumn for deposition of a polymer of said monomer onto a surface of the substrate apposed to the microcolumn; and a patterned heating block movable in conjunction with the microcolumn, wherein the heating block is apposed to the substrate, and the heating block warms solution from the microcolumn deposited on the substrate when the substrate is moved from the microcolumn towards the heating block.

13. A system for the patterned deposition of a polymer by self-assembly, the system comprising:

a polymer printhead comprising
a monomer solution reservoir and
a microcolumn fluidically coupled at a loading end to the reservoir, said microcolumn also having an elution end;

a temperature controller for regulating temperature within the microcolumn, wherein the microcolumn temperature is regulated either as a constant temperature throughout the microcolumn or as a gradient of increasing temperature from the loading end to the elution end of the microcolumn; and a substrate mounted in apposition to the elution end of the microcolumn and movable in a plane orthogonal to the axis of the microcolumn for deposition of a polymer of said monomer onto a surface of the substrate apposed to the microcolumn, wherein the gap between the elution end of the microcolumn and the substrate is less than 10 microns.

14. A system for the patterned deposition of a polymer by self-assembly, the system comprising:

a polymer printhead comprising
a monomer solution reservoir and
a microcolumn fluidically coupled at a loading end to the reservoir, said microcolumn also having an elution end;

a temperature controller for regulating temperature within the microcolumn, wherein the microcolumn temperature is regulated either as a constant temperature throughout the microcolumn or as a gradient of increasing temperature from the loading end to the elution end of the microcolumn; and a substrate mounted in apposition to the elution end of the microcolumn and movable in a plane orthogonal to the axis of the microcolumn for deposition of a polymer of said monomer onto a surface of the substrate apposed to the microcolumn, wherein the substrate comprises dialysis membrane that encloses an osmicant solution compartment.

15. A system for the patterned deposition of a polymer by self-assembly, the system comprising:

a polymer printhead comprising
a monomer solution reservoir and
a microcolumn fluidically coupled at a loading end to the reservoir, said microcolumn also having an elution end;

a temperature controller for regulating temperature within the microcolumn, wherein the microcolumn temperature is regulated either as a constant temperature throughout the microcolumn or as a gradient of increasing temperature from the loading end to the elution end of the microcolumn;

a substrate mounted in apposition to the elution end of the microcolumn and movable in a plane orthogonal to the axis of the microcolumn for deposition of a polymer of said monomer onto a surface of the substrate apposed to the microcolumn; and a second solution reservoir fluidically coupled to said microcolumn at a loading end, wherein solution entering the loading end of the microcolumn is selectable from said monomer solution reservoir or from said second solution reservoir.

* * * * *